(12) United States Patent
Shinoda et al.

(10) Patent No.: US 7,575,762 B2
(45) Date of Patent: *Aug. 18, 2009

(54) COMPOSITION COMPRISES SUSTAINED-RELEASE FINE PARTICLES AND MANUFACTURING METHOD THEREOF

(75) Inventors: Tatsuki Shinoda, Shizuoka (JP); Atsushi Maeda, Shizuoka (JP); Naoki Itou, Shizuoka (JP); Takao Mizumoto, Shizuoka (JP); Shigeru Yamazaki, Shizuoka (JP); Yuuki Takaishi, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/743,616

(22) Filed: May 2, 2007

(65) Prior Publication Data

US 2007/0202168 A1 Aug. 30, 2007

Related U.S. Application Data

(63) Continuation of application No. 10/206,010, filed on Jul. 25, 2002, now Pat. No. 7,255,876.

(60) Provisional application No. 60/308,303, filed on Jul. 27, 2001.

(51) Int. Cl.
*A61K 9/16* (2006.01)
*A61K 9/22* (2006.01)
*A61K 9/26* (2006.01)
*A61K 9/46* (2006.01)

(52) U.S. Cl. .................. 424/490; 424/466; 424/468; 424/469; 424/470; 424/493

(58) Field of Classification Search .................. None
See application file for complete search history.

(56) References Cited

U.S. PATENT DOCUMENTS

| | | | |
|---|---|---|---|
| 4,772,475 A | | 9/1988 | Fukui et al. |
| 5,437,872 A | | 8/1995 | Lee |
| 5,466,464 A | * | 11/1995 | Masaki et al. ............... 424/434 |
| 5,576,014 A | | 11/1996 | Misumoto et al. |
| 5,824,339 A | * | 10/1998 | Shimizu et al. ............... 424/466 |
| 6,495,177 B1 | * | 12/2002 | deVries et al. ............... 426/72 |
| 6,692,768 B1 | | 2/2004 | Ishibashi et al. |
| 6,872,405 B2 | * | 3/2005 | Takaishi et al. ............... 424/435 |
| 7,255,876 B2 | * | 8/2007 | Shinoda et al. ............... 424/464 |

FOREIGN PATENT DOCUMENTS

| | | | |
|---|---|---|---|
| EP | 0255725 | | 2/1988 |
| EP | 0255725 A1 | * | 2/1988 |
| EP | 0 745 382 A1 | | 12/1996 |
| EP | 0745382 A1 | * | 12/1996 |
| EP | 1125576 A1 | * | 10/1999 |
| EP | 1072256 A1 | * | 1/2001 |
| EP | 1 125 576 A1 | | 8/2001 |
| EP | 1 269 995 A1 | | 1/2003 |
| JP | 62-9 A | | 1/1987 |
| JP | 63-039811 | | 2/1988 |
| JP | 11-35451 A | | 2/1999 |
| WO | WO 99/04758 A | | 2/1999 |
| WO | WO 99/32092 A | | 7/1999 |
| WO | WO 01/72285 A | | 10/2001 |

OTHER PUBLICATIONS

Zouryu Binran, Chapter 1 General Introduction, 1975.
Sagawa, Yoshihisa; Study on Granulation by the Fluidized Bed Granulation Method (1): Preliminary Investigation on Explaining the Defects of Conventional Method and Their Improvement; Bulletin of Society of Powder Technology Japan, 1984, vol. 21, No. 4 pp. 206-211.
Sagawa, Yoshihisa; Fundamental Knowledge of Pharmaceutical Procedures 12 Technical View of Granulating: the Second Half; Pharm. Tech. Japan, 2000, vol. 16, No. 9, pp. 49-68.
Sagawa, Yoshihisa; Fundamental Knowledge of Pharmaceutical Procedures 11 Technical View of Granulating: the First Half; Pharm. Tech. Japan, 2000, vol. 16, No. 8, pp. 58-78.

* cited by examiner

*Primary Examiner*—S. Tran
(74) *Attorney, Agent, or Firm*—Townsend and Townsend and Crew LLP

(57) ABSTRACT

The present invention relates to a composition comprising sustained-release fine particles, characterized in that it contains sustained-release fine particles that can be used in quick-disintegrating tablets in the buccal cavity, one or more fillers selected from the group consisting of sugars or sugar alcohols, and one or more binders for quick-disintegrating tablets in the buccal cavity selected from the group consisting of sugars of high moldability and water-soluble polymer substances, and in that the sustained-release fine particles are granulated with filler and binder for quick-disintegrating tablets in the buccal cavity, and a manufacturing method thereof.

8 Claims, 3 Drawing Sheets

COMPOSITION COMPRISES SUSTAINED-RELEASE FINE PARTICLES AND MANUFACTURING METHOD THEREOF

CROSS-REFERENCES TO RELATED APPLICATIONS

This application is a continuation of U.S. application Ser. No. 10/206,010, filed Jul. 25, 2002, allowed, which application claims the benefit of U.S. provisional patent application No. 60/308,303 filed Jul. 27, 2001.

FIELD OF THE INVENTION

The present invention relates to a composition comprising sustained-release fine particles for quick-disintegrating tablets in the buccal cavity. In further detail, the present invention relates to a composition comprising sustained-release fine particles for quick-disintegrating tablets in the buccal cavity, characterized in that it comprises a granulation product of sustained-release fine particles and one or two or more fillers selected from the group consisting of sugars or sugar alcohols granulated with binder for quick-disintegrating tablets in the buccal cavity, and in that the ratio of ungranulated sustained-release fine particles in the entire composition is 0 to 15%.

BACKGROUND OF THE INVENTION

The "sustained-release fine particles" of the present invention means fine particles that contain a drug, have been submitted to various types of sustained-release treatments, and have a mean particle diameter of approximately 0.1 μm to approximately 350 μm. The various types of sustained-release treatments means treatment to give the quality of "sustained release" that is well known pharmaceutically. Treatment that has given gradual drug releasability, treatment that has given gastrosolubility, treatment that has given enterosolubility, treatment that has given timed releasability, treatment that has given releasability that is a combination of these, and the like, can be given as examples. Moreover, those that have been given enterosolubility are called "enteric sustained-release fine particles."

Various types of disintegrating tablets in buccal cavity were previously developed so that they could be easily taken, even without water, by persons with weak swallowing ability, including the elderly, children, and the like. Moreover, the demand for the use of an assortment of drugs in recent years has led to the need for providing the function of sustained releasability to quick-disintegrating tablets in the buccal cavity.

First-generation quick-disintegrating tablets in the buccal cavity, for instance, "Zydis™" marketed by R. P. Scherer, and the like, are known to be pharmaceutical preparations manufactured by lyophilization. These first-generation quick-disintegrating tablets in the buccal cavity are basically manufactured by lyophilization, or special drying, using a solution or suspension of the drug. Thus, the process of manufacture in a liquid state was essential, and there was no discussion of providing the function of sustained releasability.

Various second-generation quick-disintegrating tablets in the buccal cavity are known, including those that use the function of disintegrants (Japanese Kokai Patent No. Hei 10-182436, International Early Disclosure Pamphlet WO98/02185, and the like), those characterized in that a saccharide of high moldability is spray coated and/or granulated as binder on a saccharide of low moldability and which can be humidified and dried when tablet strength is further necessary (International Early Disclosure Pamphlet WO 95/20380 (corresponding U.S. Pat. No. 5,576,014, Japanese Patent No. 312141), and the like, and these are manufactured by tableting. Consideration has been given to quick-disintegrating tablets in the buccal cavity containing fine particles that have been sustained-release treated, for instance, coated by a polymer, in order to solve the apparent contradictory problem of providing the function of sustained releasability to these second-generation quick-disintegrating tablets in the buccal cavity. However, even though attempts have been made to simply mix fine particles that have been sustained-release treated with a filler for quick-disintegrating tablets in the buccal cavity and tablet this mixture, segregation occurs due to a difference in apparent specific gravity and a difference in fluidity between the filler and the sustained-release fine particles during the tableting process. The term "segregation" used here is the state where the sustained-release fine particles are not uniformly dispersed in the filler and segregation occurs when they are not uniformly dispersed. It is possible to confirm segregation by determining uniformity of content of drugs that comprise tablets once tablets have been made. For instance, it can be said that if the coefficient of variation (CV %) of the amount of drug, which is shown below, is 0 to 3.5%, segregation will not occur and if the coefficient of variation exceeds 3.5%, segregation will occur. Various problems are produced with this segregation as the cause. For instance, there are the problems of (1) tableting pressure being propagated directly to the sustained-release fine particles due to contact between the punch face and the sustained-release fine particles during tableting, or direct contact between sustained-release fine particles themselves, resulting in destruction of the sustained-release fine particles and acceleration of dissolution after they have been made into tablets, (2) the degree of destruction of the sustained-release fine particles varying with the degree of segregation and therefore, controlled dissolution, which is the design goal of sustained-release fine particle preparation, not being realized with good reproducibility after tablets are made, (3) there being fluctuations in the number of sustained-release fine particles contained in one tablet and it being impossible to guarantee uniformity of drug content, and the like.

An invention relating to a method of manufacturing spherical fine particles that are useful for manufacturing controlled-release pharmaceutical preparations that are easy to take by a special tumbling granulation method is disclosed in International Early Disclosure Pamphlet WO00/24379. This pamphlet gives a manufacturing method involving special tumbling granulation of these spherical fine particles and shows that dissolution is controlled by coating spherical fine particles and that these spherical fine particles can be used in quick-disintegrating tablets in the buccal cavity. However, our research has confirmed that the above-mentioned various problems occur and the purpose cannot be accomplished if quick-disintegrating tables in the buccal cavity simply contain spherical fine particles that have been sustained-release treated. Moreover, there is no disclosure or indication of specific means for dealing successfully with these problems in said specification.

Thus, although as yet unknown, there is a demand for introduction of quick-disintegrating tablets in the buccal cavity comprising sustained-release fine particles with which acceleration of the drug dissolution after being made into a tablet that is the result of destruction of sustained-release fine particles under tableting pressure when tablets are made is inhibited, and controlled dissolution, which is the design goal of sustained-release fine particle preparation, is realized with good reproducibility even after tablets are made, and with which uniformity of drug content is guaranteed.

BRIEF SUMMARY OF THE INVENTION

Under these circumstances, the inventors focused on studies of quick-disintegrating tablets in the buccal cavity comprising sustained-release fine particles and researched methods of preventing segregation of sustained-release fine particles and filler used in quick-disintegrating tablets in the buccal cavity, which is the source of various problems. As a result of repeating a variety of experiments, they successfully completed the present invention upon discovering that segregation of sustained-release fine particles and filler can be prevented by preparing a granulation product comprising sustained-release fine particles, several of which have aggregated together during this granulation process, using a granulation process whereby all or part of the surface of individual sustained-release fine particles is covered with filler. The "granulation" here means to make granules or powder the size and shape of which are virtually uniform. As a result of further detailed studies, it was discovered that segregation of sustained-release fine particles and filler is prevented when the ratio of ungranulated sustained-release fine particles in the entire composition that is eventually obtained is 0 to 15%. It had been thought that usually segregation readily occurs as a result of an increase in the difference in apparent specific gravity between the fine particles and filler and deterioration of fluidity of the fine particles, and the like, when several particles aggregate in this way. However, it was a complete surprise that it is possible not only to guarantee uniformity of content when making tablets, but to also simultaneously neutralize pressure during tableting by avoiding direct contact between the punch face and sustained-release fine particles, or the sustained-release fine particles themselves, and realize good reproducibility of controlled dissolution, which is the goal.

That is, the present invention relates to 1. a composition comprising sustained-release fine particles for quick-disintegrating tablets in the buccal cavity, characterized in that it comprises the product of granulation of sustained-release fine particles containing a drug and one or two or more fillers selected from the group consisting of sugars or sugar alcohols with a binder for quick-disintegrating tablets in the buccal cavity, and in that the ratio of ungranulated sustained-release fine particles in the entire composition is 0 to 15%, 2. the composition comprising sustained-release fine particles for quick-disintegrating tablets in the buccal cavity of above-mentioned 1, wherein the binder for quick-disintegrating tablets in the buccal cavity is one or two or more selected from the group consisting of saccharides of high moldability, water-soluble polymer substances, and saccharides with a low melting point, 3. the composition comprising sustained-release fine particles for quick-disintegrating tablets in the buccal cavity of above-mentioned 2, wherein the sugar or sugar alcohol is one or two or more selected from the group consisting of saccharides with low moldability, saccharides with a high melting point, and saccharides with a low melting point, 4. the composition comprising sustained-release fine particles for quick-disintegrating tablets in the buccal cavity of above-mentioned 3, wherein the mixture ratio of sustained-release fine particles, filler, and binder for quick-disintegrating tablets in the buccal cavity is 1 to 50%, 20 to 98%, and 1 to 30%, respectively, 5. the composition comprising sustained-release fine particles for quick-disintegrating tablets in the buccal cavity of above-mentioned 4, wherein the mean particle diameter of the sustained-release fine particles is approximately 0.1 μm to approximately 350 μm, 6. the composition comprising sustained-release fine particles for quick-disintegrating tablets in the buccal cavity of above-mentioned 5, wherein the sustained-release fine particles consist of at least crystal cellulose particles, drug, and polymer substance, 7. the composition comprising sustained-release fine particles for quick-disintegrating tablets in the buccal cavity of above-mentioned 6, wherein the drug is tamsulosin hydrochloride, 8. the composition comprising sustained-release fine particles for quick-disintegrating tablets in the buccal cavity of above-mentioned 7, wherein the sustained-release fine particles are enteric sustained-release fine particles, 9. the composition comprising sustained-release fine particles for quick-disintegrating tablets in the buccal cavity of above-mentioned 8, wherein the polymer substance is hydroxypropylmethyl cellulose, ethyl cellulose, Eudragit L30D55, and Eudragit NE30D, 10. the composition comprising sustained-release fine particles for quick-disintegrating tablets in the buccal cavity of above-mentioned 9, wherein the binder for quick-disintegrating tablets in the buccal cavity is one or two or more selected from the group consisting of maltose, trehalose, sorbitol, and maltitol, 11. quick-disintegrating tablets in the buccal cavity consisting of the composition comprising sustained-release fine particles of above-mentioned 10, 12. the quick-disintegrating tablets in the buccal cavity of above-mentioned 11, characterized in that the coefficient of variation (CV %) of the amount of drug, which is an indicator of uniformity of content, is 3.5% or less, 13. a method of manufacturing a composition comprising sustained-release fine particles for quick-disintegrating tablets in the buccal cavity, characterized in that it comprises the product of granulation of sustained-release fine particles containing a drug and one or two or more fillers selected from the group consisting of sugars or sugar alcohols with a binder for quick-disintegrating tablets in the buccal cavity, and in that the ratio of ungranulated sustained-release fine particles in the entire composition is 0 to 15%, 14. the method of manufacturing a composition comprising sustained-release fine particles for quick-disintegrating tablets in the buccal cavity of above-mentioned 13, wherein the binder for quick-disintegrating tablets in the buccal cavity is one or two or more selected from the group consisting of saccharides of high moldability, water-soluble polymer substances, and saccharides with a low melting point, 15. the method of manufacturing a composition comprising sustained-release fine particles for quick-disintegrating tablets in the buccal cavity of above-mentioned 14, wherein the sugar or sugar alcohol is one or two or more selected from the group consisting of saccharides with low moldability, saccharides with a high melting point, and saccharides with a low melting point, 16. the method of manufacturing a composition comprising sustained-release fine particles for quick-disintegrating tablets in the buccal cavity of above-mentioned 15, wherein the mixture ratio of sustained-release fine particles, filler, and binder for quick-disintegrating tablets in the buccal cavity is 1 to 50%, 20 to 98%, and 1 to 30%, respectively, 17. the method of manufacturing a composition comprising sustained-release fine particles for quick-disintegrating tablets in the buccal cavity of above-mentioned 16, wherein the mean particle diameter of the sustained-release fine particles is approximately 0.1 μm to approximately 350 μm, 18. the method of manufacturing a composition comprising sustained-release fine particles for quick-disintegrating tablets in the buccal cavity of above-mentioned 17, wherein the sustained-release fine particles consist of at least crystal cellulose particles, drug, and polymer substance, 19. the method of manufacturing a composition comprising sustained-release fine particles for quick-disintegrating tablets in the buccal cavity of above-mentioned 18, wherein the drug is tamsulosin hydrochloride, 20. the method of manufacturing composition comprising sustained-release fine particles for quick-disintegrating tablets in the buccal cavity of above-mentioned 19, wherein the sustained-release fine particles are enteric sustained-release fine particles, 21. the method of manufacturing a composition comprising sustained-release fine particles for quick-disintegrating tablets in the buccal cavity of above-mentioned 20, wherein the polymer substance is hydroxypropylmethyl cellulose, ethyl cellulose, Eudragit L30D55, and Eudragit NE30D, 22. the method of manufacturing a composition comprising sustained-release fine particles for quick-disintegrating tablets in the buccal cavity of above-mentioned 21, wherein the binder for quick-disintegrating tablets in the buccal cavity is one or two or more selected from the group consisting of maltose, trehalose, sorbitol, and maltitol, 23. a method of manufacturing quick-disintegrating tablets in the buccal cavity consisting of the composition comprising sustained-release fine particles of above-mentioned 22, and 24. the method of manufacturing quick-disintegrating tablets in the buccal cavity of above-mentioned 23, characterized in that the coefficient of variation (CV %) of the amount of drug, which is an indicator of uniformity of content, is 3.5% or less.

The "binder for quick-disintegrating tablets in the buccal cavity" of the present invention means of binders that are generally used, a binder that is particularly useful in the preparation of quick-disintegrating tablets in the buccal cavity, and a variety is selected in relationship with the "filler" of the present invention. The details are described below, including its embodiments.

The "ungranulated sustained-release fine particles" in the present invention means sustained-release fine particles that do not comprise granulation product when sustained-release fine particles are granulated together with filler using a binder for quick-disintegrating tablets in the buccal cavity. Moreover, the ratio of "ungranulated sustained-release fine particles" is calculated by the following formulas using the values from determination of particle diameter distribution of the sustained-release fine particles and quantitative ratio by particle diameter of the composition comprising sustained-release fine particles by the following methods:

Ratio of ungranulated sustained-release fine particles (%)=$G_1+\Sigma(G_{i+1}-(P_i-G_i))$ Here, the estimation of $\Sigma$ is obtained by calculation from i=1 and estimating the value up to the point before $(G_{i+1}-(P_i-G_i))$ becomes negative.

$P_1$: sustained-release fine particle ratio on sieve with smallest opening size within the particle diameter distribution of the sustained-release fine particles (with the exception of that where it is 0%).

$P_2$: sustained-release fine particle ratio on sieve with second smallest opening size within particle diameter distribution of the sustained-release fine particles (with the exception of that where it is 0%). The third, fourth and so on are referred to as $P_3$, $P_4$, and so on, and they are as a whole represented as $P_1$.

$G_1$: value of quantitative ratio by particle diameter distribution of composition on sieve with the same opening size as $P_1$.

$G_2$: value of quantitative ratio by particle diameter distribution of composition on sieve with same opening size as $P_2$; the third, fourth, and so on are referred to as $G_3$, $G_4$, and so on, and they are as a whole represented as $G_1$.

The "the ratio of ungranulated sustained-release fine particles in the total composition is brought to 15% or less" in the present invention in other words means that the ratio of sustained-release fine particles that are not granulated is low, that is, the majority of sustained-release fine particles are contained in each granulation product. Moreover, it also means that segregation of sustained-release fine particles and filler is inhibited.

"Granulation product" in the present invention means a granulation product consisting of sustained-release fine particles, filler, and binder for quick-disintegrating tablets in the buccal cavity, and granulation product that does not comprise sustained-release fine particles is defined in particular as "granulation product that does not comprise sustained-release fine particles." That is, the specific form of the composition of the present invention is a mixture comprising "granulation product," "ungranulated sustained-release fine particles," and "granulation product that does not comprise sustained-release fine particles."

Moreover, the quick-disintegrating tablets in the buccal cavity in the present invention indicates tablets with which disintegration time in the buccal cavity is 0 to 2 minutes, preferably 0 to 1 minute, and can be those disclosed in International Early Disclosure Pamphlet WO98/02185, International Early Disclosure Pamphlet WO95/20380, Kokai Patent No. Hei 10-182436, U.S. patent application Ser. No. 10/142, 081 (corresponding International Patent Application No. PCT/JP02/04481), and the like.

Moreover, the "acceleration of dissolution of sustained-release fine particles is inhibited" and "controlled dissolution, which is the goal [of sustained-release fine particles], is realized" in the present invention means that there is not a difference between the dissolution rate of the sustained-release fine particles and the dissolution rate of the quick-disintegrating tablets in the buccal cavity. Specifically, when dissolution tests of sustained-release fine particles and quick-disintegrating tablets in the buccal cavity comprising the sustained-release fine particles are performed and drug dissolution of the sustained-release fine particles is compared, the difference between the dissolution rate of sustained-release fine particles and the dissolution rate of quick-disintegrating tablets in the buccal cavity is 0 to 15% at each dissolution time where drug dissolution of sustained-release fine particles is approximately 30%, approximately 50%, and approximately 80%. If the sustained-release fine particles are enteric sustained-release fine particles, the above-mentioned evaluation cannot be performed under conditions of a pH of 1.2, the difference between the dissolution rate of the enteric sustained-release fine particles and the dissolution rate of quick-disintegrating tablets in the buccal cavity two hours after starting the dissolution experiment is 0 to 10%.

Moreover, "good reproducibility" means that the same results are obtained, for instance, even with quick-disintegrating tablets in the buccal cavity prepared on a different occasion, when the difference between dissolution of quick-disintegrating tablets in the buccal cavity and dissolution of sustained-release fine particles comprising these tablets is compared as described above.

Moreover, the "coefficient of variation (CV %) of the amount of drug" in the present invention is an indicator of uniformity of content. Tests of uniformity of content described below are conducted and the CV % is calculated by the following formula:

$$CV\% = (\text{standard deviation of each content})/(\text{mean content}) \times 100$$

A "CV % of 0 to 3.5%" can be regarded as no segregation with few fluctuations in drug content of the tablets that have been prepared, and it can be said that "uniformity of drug content is guaranteed." Moreover, a "CV % exceeding 3.5%" can be regarded as segregation with large fluctuations in drug content, and it can be said that "uniformity of content is poor." Incidentally, a "CV % of 0 to 3.5%" is the appropriate range of the coefficient of variation in the present invention, the number that appears to be necessary for quality assurance and indicates that a composition with a constant drug content is obtained.

The composition comprising sustained-release fine particles of the present invention and manufacturing method thereof of the present invention will now be described in detail.

There are no particular restrictions to the drug used in the present invention as long as it is an active component requiring sustained releasability that is effective in terms of treatment or that is effective in terms of prevention. Examples of this drug are hypnotic sedatives, sleep-inducing agents, anti-anxiety drugs, anti-epilepsy drugs, antidepressants, anti-Parkinson's drugs, psychoneurotic drugs, central nervous system drugs, local anesthetics, skeletal muscle relaxants, autonomic nerve drugs, antipyretic analgesic anti-inflammatory agents, antispasmodics, anti-vertigo drugs, cardiotonics, drugs for arrhythmia, diuretics, hypotensives, vasoconstrictors, vasodilators, drugs for the circulatory system, drugs for hyperlipidemia, drugs to promote respiration, antitussives, expectorants, antitussive expectorants, bronchodilators, antidiarrheal agents, drugs for controlling intestinal function, drugs for peptic ulcer, stomachics, antacids, laxatives, cholagogues, gastrointestinal drugs, adrenocortical hormones, hormones, urogenital drugs, vitamins, hemostatics, drugs for liver disease, drugs used for gout, drugs used for diabetes, antihistamines, antibiotics, antibacterials, drugs used against malignant tumors, chemotherapeutic drugs, multisymptom cold medications, nutrition-enhancing health drugs, osteoporosis drugs, and the like. Examples of these drugs are anti-inflammatory, antipyretic antispasmodics or analgesics, such as indomethacin, diclofenac, diclofenac sodium, codeine, ibuprofen, phenylbutazone, oxyfenbutazone, mepirizole, aspirin, idensamide, acetaminophen, aminopyrine, phenacetin, butyl scopolamine bromide, morphine, etomidoline, pentazocine, fenoprofen calcium, naproxen, celecoxib, vardecoxib, tramadole, and the like, anti-rheumatic drugs, such as etodolac, and the like, anti-tuberculosis drugs, such as isoniazide, ethambutol chloride, and the like, drugs for the circulatory system, such as isosorbid nitrate, nitroglycerin, nifedipine, bardnidipine hydrochloride, nicardipine hydrochloride, dipyridamile, amrinone, indenolol hydrochloride, hydralazine hydrochloride, methyl dopa, furosemide, spironolactone, guanetidine nitrate, resperine, amosulalol hydrochloride, lisinoopril, methoprolol, pilocarbpine, tasosartan, and the like, psychoneurotic drugs, such as chlorpromazine hydrochloride, amitriptyline hydrochloride, nemonapride, haloperidole, moperone hydrochloride, perphenazine, diazepam, lorazepam, chlordiazepoxide, adinazolam, alprazolam, methylphenidate, milnasivran, peroxetin, risperidone, sodium valproate, and the like, antiemetics, such as methoclopramide, ramosetron hydrochloride, granisetron hydrochloride, ondansetron hydrochloride, azasetron hydrochloride, and the like, antihistamines, such as chlorpheniramine maleate, diphenhydramine hydrochloride, and the like, vitamins, such as thiamine nitrate, tocopherol hydrochloride, sicotiamine, pyridoxal phosphate, cobamamide, ascorbic acid, nicotinamide, and the like, antigout drugs, such as allopurinol, colchicine, probenamide, and the like, anti-Parkinson's drugs, such as levo dopa, selegiline, and the like, hypnotic sedatives, such as amobarbital, bromwarelyl urea, midazolam, chloral hydrate, and the like, anti-malignant tumor drugs, such as fluorouracil, carmofur, aclarubicin hydrochloride, cyclophosphamide, thiotepa, and the like, anti-allergy drugs, such as pseudoephedrine, terfenadine, and the like, antidepressants, such as phenyl propanolamine, ephedrins, and the like, drugs used to treat diabetes, such as acethexamide, insulin, torbutamide, desmopressine, glibizide, and the like, diuretics, such as hydrochlorthiazide, polythiazide, triaterene, and the like, bronchodilators, such as aminophyllin, formoterol fumarate, theophylline, and the like, antitussives, such as codeine phosphate, noscapine, dimemorphan phosphate, dextromethorphan, and the like, antiarrythmia drugs, such as quinidine nitrate, digitoxin, propafenone hydrochloride, procainamide, and the like, surface anesthetics, such as aminoethyl benzoate, lidocaine, dibucaine hydrochloride, and the like, antiepilepsy drugs, such as phenytoin, etosuccimide, primidone, and the like, synthetic corticosteroids, such as hydrocortisone, prednisone, triamcinolone, betamethasone, and the like, drugs for the digestive tract, such as famotidine, ranitidine hydrochloride, dimethisone, sucralfate, sulpiride, tepronone, praunotol, 5-aminosalicylic acid, sulfasalazine, omeprazole, lannoprazole, and the like, drugs for the central nervous system, such as indeloxazine, idebenone, thiapride hydrochloride, bifermerane hydrochloride, calcium homopanthothenate, and the like, agents for treatment of hyperlipidemia, such as pravastatin sodium, sinvastatin, lovastatin, prevastatin, atorvastatin, and the like, antibiotics, such as ampicillin phthalizyl hydrochloride, cefotetan, josamycin, and the like, BPH therapeutic agents, such as tamsulosin hydrochloride, doxazocin mesilate, terazosine hydrochloride, and the like, anti-asthma drugs, such as pranrucast, zafirlukast, albuterol, ambrozole, budesonide, leverbuterol, and the like, prostaglandin I derivative agents for improving peripheral circulation, such as beraprost sodium, and the like, antithrombotics, hypotensives, agents for treatment of heart failure, agents for treatment of various complications of diabetes, agents for treatment of peptic ulcer, agents for treatment of skin ulcers, agents for treatment of hyperlipidemia, anti-asthma agents, and the like. The drug can be used in free form or as any salt that is pharmaceutically acceptable.

Moreover, the present invention can comprise drugs that do not require sustained-releasability. Furthermore, one or a combination of two or more drugs can be used. There are no special restrictions to the amount of this drug as long as it is the amount that is usually effective for treatment, but it is preferably 50 w/w % or less, preferably 20 w/w % or less, in terms of tablet weight. For instance, when it exceeds 50 w/w % in terms of tablet weight, the ratio of fine particles to filler is high and granulation by the filler will be insufficient.

These drugs are sustained-release treated and contained in the sustained-release fine particles as fine particles with which release of the drug is controlled by the conventional methods described below. There are no special restrictions to the particle diameter of the sustained-release fine particles as long as it is within a range with which there is not a gritty feeling in the buccal cavity. Usually approximately 0.1 µm to approximately 350 µm is preferred, approximately 5 µm to approximately 250 µm is more preferred, and approximately 50 µm to approximately 250 µm is further preferred as the mean particle diameter. If it is smaller than 0.1 µm, it will be difficult to provide sustained releasability with the current pharmaceutical technology, while if it is larger than 350 µm, it will have a very uncomfortable feeling, such as a gritty feeling, in the buccal cavity.

Moreover, the sustained-release fine particles of the present invention can be prepared by conventional methods. For instance, sustained-release fine particles can be made by the agitation granulation method or tumbling fluidized granulation method after adding polymer solution to drug and microcrystalline cellulose, as disclosed in Japanese Patent No. Hei 7-72129 (corresponding U.S. Pat. No. 4,772,475) and International Early Disclosure Pamphlet WO00/24379, or sustained-release fine particles can be made by layering and coating drug over commercial microcrystalline cellulose particles (avicel particles, Asahi Kasei, brand name Celphere 102, and the like) as the core by conventional coating methods, such as fluidized bed coating, tumbling fluidized coating, and the like, and then further coating with polymer substance to form a controlled-release film (Avicel Jiho, No. 40, P. 16-33, Asahi Kasei Corp.). Moreover, it is also possible to use a conventional crystalline filler of approximately 1 µm~approximately 150 µm, specifically crystalline lactose, granular sugar, sodium chloride, corn starch, silicon dioxide (silica gel), and the like, taking into consideration the size of the sustained-release fine particles (approximately 0.1 to approximately 350 µm). Pre-coating with water-soluble polymer substance, water-insoluble polymer substance, and the like, can also be used in order to round the edges of the filler, which becomes the core, in this case. In addition, it is also possible to make sustained-release fine particles by spray drying a solution or suspension of drug and polymer substance using appropriate equipment, such as a spray dryer, and the like. Examples of solvents used to prepare these sustained-release fine particles are water, organic solvent, and the like. Examples of organic solvents are alcohols, specifically, methanol, ethanol, propanol, isopropanol, and the like, halogenated alkanes, specifically dichloromethane, chloroform, chloroethane, trichloroethane, carbon tetrachloride, and the like, ketones, specifically acetone, methyl ethyl ketone, and the like, nitrites, specifically acetonitrile, and the like, and hydrocarbons, specifically n-hexane, cyclohexane, and the like. One or a mixture at an appropriate ratio of two or more of these organic solvents can be used, and they can also be used as a mixture with water at an appropriate percentage.

The polymer substance used to prepare the sustained-release fine particles can be selected as needed in accordance with the purpose of use. Examples are water-insoluble polymers, gastrosoluble polymers, enterosoluble polymers, wax-like substances, and the like. Examples of water-insoluble polymers are water-insoluble cellulose ether, such as ethyl cellulose, Aquacoat (brand name, Asahi Kasei), and the like, water-insoluble acrylic acid copolymers, such as ethyl acrylate-methyl methacrylate-trimethyl ammonium chloride ethyl methacrylate copolymer (for instance, brand name of Eudragit RS, Röhm), methyl methacrylate-ethyl acrylate copolymer dispersion (for instance, brand name: Eudragit NE30D, Röhm), and the like, and the like. Examples of gastrosoluble polymers are gastrosoluble polyvinyl derivatives, such as polyvinyl acetal diethyl aminoacetate, and the like, gastrosoluble acrylic acid copolymers such as methyl methacrylate-butyl methacrylate-dimethylaminoethyl methacrylate copolymer (for instance, brand name Eudragit E, Röhm), and the like, and the like. Examples of enterosoluble polymers are enterosoluble cellulose derivatives, such as hydroxypropylmethyl cellulose acetate succinate, hydroxypropyl methyl cellulose phthalate, hydroxymethyl ethyl cellulose phthalate, carboxymethyl ethyl cellulose, and the like, enterosoluble acrylic acid copolymers, such as methacrylic acid-methyl methacrylate copolymer (for instance, brand name: Eudragit L100, Eudragit S, both by Röhm), methacrylic acid-ethyl acrylate copolymer (for instance, brand name of Eudragit L100-55, Eudragit L30D55, Röhm), and the like, and the like. Examples of wax-like substances are solid oils and fats, such as hydrogenated castor oil, hydrogenated coconut oil, tallow, and the like, higher fatty acids, such as stearic acid, lauric acid, myristic acid, palmitic acid, and the like, and higher alcohols, such as cetyl alcohol, stearyl alcohol, and the like. Of these, methacrylic acid-ethyl acrylate copolymer is preferred for providing enterosolubility and pH-independent water-insoluble polymer, particularly ethyl cellulose, is preferred for providing sustained release whereby a drug is released gradually. One or an appropriate combination of two or more of these polymer substances can be used for the goal of controlled dissolution.

Furthermore, plasticizer can also be added as needed. Examples of this plasticizer are triacetin, triethyl citrate, dibutyl sebacate, acetylated monoglyceride, ethyl acrylate-methyl methacrylate copolymer dispersion (for instance brand name: Eudragit NE30D, Röhm), and the like, and triacetin and ethyl acrylate-methyl methacrylate copolymer dispersion are preferred.

Moreover, water-soluble polymers, saccharides, salts, and the like, can be mixed with the above-mentioned polymer substances, such as water-insoluble polymers, gastrosoluble polymers, enterosoluble polymers, and the like, or wax-like substances, and the like. Examples of these substances are hydroxypropylcellulose, hydroxypropylmethyl cellulose, polyvinyl pyrrolidone, polyvinyl alcohol, and the like, as water-soluble polymer substances. Examples of saccharides are maltose, maltitol, and the like, and examples of salts are sodium chloride, and the like. The amount of polymer and saccharide used here can be adjusted as needed in order to control the dissolution speed of the drug. Moreover, one or a combination of two or more of these polymers and saccharides can be used. Incidentally, the water-soluble polymer substances, saccharides, and salts used here are added in order to easily control dissolution of drug from the sustained-release fine particles, and they should be differentiated from those that are used in preparation of the composition of the present invention.

There are no special restrictions to the "filler" used in the present invention as long as it is a pharmaceutically acceptable sugar or sugar alcohol. Examples of sugar or sugar alcohol are saccharides of low moldability disclosed in International Early Disclosure Pamphlet WO95/20380. Specific examples are xylitol, erythritol, glucose, mannitol, sucrose, and lactose. Of these, mannitol, lactose, and erythritol are preferred. In addition, one or a combination of two or more of these saccharides can be used. The "saccharide of low moldability" here means one that, for instance, shows a tablet hardness of less than 2 kp when 150 mg saccharide are tableted under a tableting pressure of 10 to 50 kg/cm$^2$ using a punch with a diameter of 8 mm (refer to WO95/20380 (corresponding U.S. Pat. No. 5,576,014, Japanese Patent No. 3122141). Moreover, sugars with a high melting point and sugars with a low melting point in U.S. patent application Ser.

No. 10/142,081 (corresponding International Patent Application No. PCT/JP02/04481) can also be selected.

There are no special restrictions to the saccharide with a low melting point used in the present invention as long as it is pharmaceutically acceptable and it is a saccharide with a low melting point listed in U.S. patent application Ser. No. 10/142,081 (corresponding International Patent Application No. PCT/JP02/04481) and it has a relatively lower melting point than the drugs and saccharides with a high melting point used in the present invention, but a saccharide with a melting point of approximately 80 to approximately 180° C. is preferred and a saccharide [with a melting point] of approximately 90 to 150° C. is further preferred. Examples of this saccharide are glucose (monohydrate, melting point of 83° C.), xylitol (melting point of 93° C.), trehalose (dihydrate, melting point of 97° C.), sorbitol (hydrate, melting point of a little less than 100° C.), maltose (melting point of 102° C.), sorbitol (melting point of 110° C.), erythritol (melting point of 122° C.), glucose (melting point of 146° C.), maltitol (melting point of 150° C.), mannitol (melting point of 166° C.), sucrose (melting point of approximately 170° C.), and the like. One or two or more saccharides selected from the group consisting of these can be used. Of these saccharides, one or two or more saccharides selected from glucose, xylitol, trehalose, sorbitol, maltose, erythritol, maltitol, and their hydrates are preferred. Trehalose, maltose, erythritol, or maltitol, particularly trehalose and/or erythritol, are ideal because these saccharides themselves are only slightly moisture-absorbing and therefore are easy to handle. One or a combination of two ore more of these saccharides can be used. These saccharides also can be used as a hydrate. When the hydrate and anhydride of the saccharide have different melting points, the heating temperature should be set accordingly as needed.

The "saccharide with a high melting point" used in the present invention is a saccharide with a high melting point listed in U.S. patent application Ser. No. 10/142,081 (corresponding Patent Application No. PCT/JP02/04481). It is a saccharide whose melting point temperature difference from the saccharide with a low melting point used in the present invention is 10° C. or higher, further preferably, a saccharide with a melting point temperature difference of 20° C. or higher. Taking into consideration the difference between the temperature at which the heating device is set and the temperature of the tablet, which is the object to be heated, it is preferred that saccharides with a greater difference between their melting points be selected. Specifically, xylitol (melting point of 93° C.), trehalose (dihydrate, melting point of 97° C.), sorbitol (hydrate, melting point of a little less than 100° C.), maltose (melting point of 102° C.), sorbitol (melting point of 110° C.), erythritol (melting point of 122° C.), glucose (melting point of 146° C.), maltitol (melting point of 150° C.), mannitol (melting point of 166° C.), sucrose (melting point of approximately 170° C.), lactose (melting point of 202° C.), and the like, are given. One or two or more saccharides selected from the group consisting of these can be used. Illustration of saccharides with a high melting point virtually duplicates the saccharides with a low melting point, but because a "a saccharide with a high melting point" is selected in terms of a relative relationship with the saccharide with a low melting point, the same saccharides are not selected. The "saccharides with a high melting point" and "saccharides with a low melting point" of the present invention are selected as needed taking into consideration the chemical properties of the drug that will be used, that is, stability of the drug with respect to temperature. When the relationship between the "saccharide with a high melting point" and the "saccharide with a low melting point" is described in specific terms, xylitol, trehalose, sorbitol, erythritol, glucose, maltitol, mannitol, sucrose, lactose, and their hydrates can be used as the "saccharide with a high melting point" when glucose (monohydrate, melting point of 83° C.) is used as the "saccharide with a low melting point" that is used in the present invention. Moreover, sorbitol, erythritol, glucose, maltitol, mannitol, sucrose, lactose, and their hydrates can be used as the "saccharide with a high melting point" when xylitol (melting point of 93° C.) or trehalose (dihydrate, 97° C.) is used as the "saccharide with a low melting point" that is used in the present invention. Glucose, maltitol, mannitol, sucrose or lactose can be used as "the saccharide with a high melting point" when erythritol (melting point of 122° C.) is used as the "saccharide with a low melting point" that is used in the present invention. Furthermore, mannitol, sucrose or lactose can be used as the "saccharide with a high melting point" when maltitol (melting point of 150° C.) is used as the "saccharide with a low melting point" in the present invention. In addition, lactose can be used as the "saccharide with a high melting point" when sucrose (melting point of approximately 170° C.) is used as the "saccharide with a low melting point" in the present invention. The "saccharide with a high melting point" is selected as described, as necessary in accordance with the type of saccharide used in the present invention. When selecting the saccharides so that there is a greater difference between their melting points, the "saccharide with a high melting point" is preferably one or two or more saccharides selected from the group consisting of glucose, maltitol, mannitol, sucrose and lactose, and further preferably mannitol, sucrose, and lactose. These are used in the appropriate amounts of one or a mixture of two or more as needed.

The saccharides of high moldability listed in International Early Disclosure Pamphlet WO95/20380, the saccharides with a low melting point listed in U.S. patent application Ser. No. 10/142,081 (corresponding International Patent Application PCT/JP02/04481), or water-soluble polymer substances are selected as the "binder for quick-disintegrating tablets in the buccal cavity" used in the present invention. For instance, maltose (preferably malt syrup powder (maltose content of 83% or higher)), trehalose, sorbitol, or maltitol are given as saccharides of high moldability, and maltose and trehalose are preferred. The "saccharide of high moldability" here means one that shows a tablet hardness of 2 kp or more when 150 mg saccharide are tableted under a tableting pressure of 10 to 50 kg/cm$^2$ using a punch with a diameter of 8 mm (refer to WO 95/20380 (corresponding U.S. Pat. No. 5,576,014, Japanese Patent No. 3122141). The above-mentioned saccharides with a low melting point are given as saccharides with a low melting point. Moreover, hydroxypropyl cellulose, hydroxypropylmethyl cellulose, polyvinyl pyrrolidone, copolyvidone, polyvinyl alcohol, and the like, are given as water-soluble polymer substances. One or a combination of two or more "binder for quick-disintegrating tablets in the buccal cavity" can be used. Hydroxypropyl cellulose, hydroxypropylmethyl cellulose, or copolyvidone with low hygroscopicity are preferred taking into consideration the environment during storage as a starting material and a pharmaceutical preparation, and copolyvidone is ideal.

In addition, the "binder for quick-disintegrating tablets in the buccal cavity" of the present invention can be one or two or more selected from the group consisting of "saccharides of high moldability," "saccharides with a low melting point," and "water-soluble polymer substances."

I. "Filler": saccharide of low moldability, "binder for quick-disintegrating tablets in the buccal cavity": saccharide of high moldability, or water-soluble polymer substance, II. "Filler": saccharide with a high melting point, "binder for quick-disintegrating tablets in the buccal cavity": saccharide with a low melting point, III. "Filler": saccharide with a high melting point, "binder for quick-disintegrating tablets in the buccal cavity": saccharide with a low melting point, and water-soluble polymer substance, and IV. "Filler": saccharide with a high melting point and saccharide with a low melting point, "binder for quick-disintegrating tablets in the buccal cavity": water-soluble polymer substance or saccharide of high moldability are given as specific embodiments of the present invention relating to selection of the above-mentioned "filler" and "binder for quick-disintegrating tablets in the buccal cavity." As a specific illustration of IV, it is preferred that erythritol is selected as the "saccharide with a low melting point," lactose and/or mannitol are selected as the "saccharide with a high melting point," and maltitol is further selected as the binder for quick-disintegrating tablets in the buccal cavity ("saccharide of high moldability"), or that erythritol is selected as the "saccharide with a low melting point," lactose and/or mannitol are selected as the "saccharide with a high melting point," and copolyvidone is further selected as the binder for quick-disintegrating tablets in the buccal cavity ("water-soluble polymer").

The amount of "filler" used in the present invention is adjusted as needed in accordance with the dose of the drug and/or the size of the tablets. This amount added is adjusted as needed by increasing the amount of "filler" used in the present invention when the dose of drug is small and by reducing the amount of "filler" used in the present invention when the dose of drug is large, and the like, to obtain tablets of the desired size. It is usually preferably 20 to 1,000 mg, further preferably 50 to 500 mg, even more preferably 100 to 400 mg, per tablet. There is a chance that thorough granulation cannot be realized if the amount of filler added is less than 20 mg. Moreover, the amount of filler to the amount of saliva in the buccal cavity will be too great when [the amount of filler added] is more than 1,000 mg, and an uncomfortable feeling will be produced when it is in the mouth.

The amount of "binder for quick-disintegrating tablets in the buccal cavity" that is used in the present invention is usually preferably 0.5 to 50 w/w %, further preferably 1 to 30 w/w %, even more preferably 1 to 20 w/w %, per weight of "filler" used in the present invention. If it is less than 0.5 w/w % per the weight of "filler," there is a chance that function as a binder will not be realized in full. Moreover, if there is more than 50 w/w % per the weight of "filler," there is a possibility that many problems, including delayed disintegration, and the like, will occur and good properties will not be obtained when used as a quick-disintegrating tablet in the buccal cavity. Although the mixture ratio of "sustained-release fine particles," "filler," and "binder for quick-disintegrating tablets in the buccal cavity" should not be definitively set forth by their percentages, when an illustration is given, their respective mixture ratio is preferably 1 to 50%, 20 to 98%, and 1 to 30%, more preferably 1 to 20%, 60 to 98%, and 1 to 20%.

In addition to the "filler" and "binder for quick-disintegrating tablets in the buccal cavity" that are used in the present invention, it is possible to add a variety of additives that are pharmaceutically acceptable and are used as additives. These additives can be mixed with the filler when the sustained-release fine particles are granulated, or they can be used as a mixture with the composition of the present invention when tablets are made. Examples of these additives are disintegrants, sour flavorings, foaming agents, artificial sweeteners, fragrances, lubricants, coloring agents, stabilizers, and the like. One or a combination of two or more of these additives can be used. Moreover, there are no particular restrictions to the amount added as long as it is the amount normally pharmaceutically used by persons in the field and it is within a range with which the results of the present invention are not compromised.

Examples of disintegrants are starches, such as corn starch, and the like, carmellose calcium, partially alpha-converted starch, crospovidon, lower-substituted hydroxypropyl cellulose, and the like. Examples of sour flavoring are citric acid, tartaric acid, malic acid, and the like. Examples of foaming agents are sodium bicarbonate, and the like. Examples of artificial sweeteners are saccharine sodium, glycyrrhizinate dipotassium, aspartame, stevia, sormatin, and the like. Examples of fragrances are lemon, lemon-lime, orange, menthol, and the like. Examples of lubricants are magnesium stearate, calcium stearate, sucrose fatty acid ester, polyethylene glycol, talc, stearic acid, and the like. Examples of coloring agents are food coloring, such as yellow food dye No. 5, red food dye No. 2, blue food dye No. 2, and the like; food lake coloring; iron oxide red, and the like. Stabilizers are selected by drug after performing various tests. One or a combination of two or more of these additives can be added in an appropriate amount as needed.

The processes of the method of manufacturing the composition comprising sustained-release fine particles of the present invention, particularly the manufacturing conditions, and the like, will now be described in detail:

The method of manufacturing the composition comprising sustained-release fine particles for quick-disintegrating tablets in the buccal cavity of the present invention will now be described using (a) the process of manufacturing sustained-release fine particles comprising the amount of drug that is effective in terms of treatment or prevention and with which the speed of dissolution of this drug is controlled and (b) the process whereby "sustained-release fine particles" and "filler" are granulated with "binder for quick-disintegrating tablets in the buccal cavity."

Process (a): Process of Manufacture of Sustained-Release Fine Particles

The sustained-release fine particles are made by conventional methods, as previously mentioned. There are no particular restrictions to this method and it can be selected as needed as long as it is one with which the goal of controlled dissolution is obtained. For instance, drug is layered and coated on commercial crystalline cellulose particles, crystalline lactose, granular sugar, sodium chloride, silicon dioxide, and the like, using a binder such as hydroxypropylmethyl cellulose, and the like, and then a polymer substance, such as water-insoluble polymer substance, gastrosoluble polymer substance, enterosoluble polymer substance, wax-like substance, and the like, is further coated on this to make sustained-release fine particles. It is also possible to layer and coat a polymer substance, such as water-insoluble polymer substance, gastrosoluble polymer substance, enterosoluble polymer substance, wax-like substance, and the like, together with drug on commercial crystalline cellulose particles, crystalline lactose, granular sugar, sodium chloride, silicon dioxide, and the like to make sustained-release fine particles. Sustained-release fine particles are also made by the agitation granulation method or tumbling fluidized granulation method after adding a solution of polymer substance to drug and microcrystalline cellulose. The above-mentioned coating can be further performed on these sustained-release fine particles, and they can be given enterosoluble function by coating with enterosoluble polymer base as necessary. A fluidized bed granulator, and the like, for instance, is selected for coating. Temperature, and further, the spraying liquid volume, spraying air volume, and the like, are set so that the product temperature is approximately 40° C. to approximately 60° C. in the case of coating using water and at approximately 30° C. to approximately 60° C. when an organic solvent is used. The concentration of drug, percentage and amount of polymer substance, and the like, used for the coating can be adjusted as needed in accordance with the desired speed of dissolution.

Process (b): Granulation Process

There are no special restrictions to the granulation method of the present invention as long as it is one with which the sustained-release fine particles have been granulated with "filler" and "binder for quick-disintegrating tablets in the buccal cavity". For example, fluidized bed granulation, agitation granulation, tumbling granulation, and the like, can be selected as this granulation method. Of these, the fluidized bed granulation method is preferred in terms of productivity. The method whereby a solution of the "binder for quick-disintegrating tablets in the buccal cavity" that is used in the present invention dissolved and/or suspended in a pharmaceutically acceptable solvent is sprayed onto a mixture of sustained-release fine particles and "filler" to make granules and prepare the "composition" can be selected for the fluidized bed granulation method. The sustained-release fine particles should be covered with "filler" at this time. The manufacture conditions are preferably, for instance, a product temperature of approximately 25° C. to approximately 40° C. and a water content of approximately 0.2 to approximately 5%. Moreover, granulation by intermittent spraying is preferred. "Intermittent spraying" means interrupted spraying and is the method of spraying for granulation whereby, for instance, cycles of spraying for 10 seconds following by drying for 30 seconds, and the like, are repeated. Moreover, this cycle can be set as needed for manufacture. In addition, the spray time-dry time can be selected appropriately. It is also possible to granulate after adding the above-mentioned additives as needed.

The "filler" can be a commercial product used as is. When mean particle diameter of the "filler" is larger than the mean particle diameter of the sustained-release fine particles, it is preferred that the "filler" be pulverized using an appropriate pulverizing device, such as hammer mill, sample mill, pin mill, and the like, in order to facilitate granulation with the sustained-release particles. It is preferred that the "binder for quick-disintegrating tablets in the buccal cavity" be dissolved in water to obtain a solution when it is a saccharide of high moldability. This liquid concentration should be, for instance, 10 to 40 w/w %, more preferably 20 to 30 w/w %, in order to maximize binding ability of the binder for quick-disintegrating tablets in the buccal cavity. If liquid concentration is lower than 10 w/w %, the liquid volume will be too great and the procedure will take more time, while if the liquid concentration is higher than 40 w/w %, the procedure will be completed in a shorter amount of time and it will therefore be difficult to maintain the spraying time-drying time cycle.

Moreover, the composition comprising sustained-release fine particles of the present invention can be used in the quick-disintegrating tablets in the buccal cavity, and this method comprises (c): the process of making tablets by tableting the composition obtained in process (b) and (d): the process of humidifying and drying the tablets obtained in process (c) as necessary. Furthermore, when the above-mentioned saccharide with a high melting point and saccharide with a low melting point have been selected for the composition, it is possible to select the method consisting of process (d'): the process of heating the tablets obtained by process (c), and (e): the process of cooling after process (d'). Process (d) can also be performed after processes (d') and (e).

Process (c): Tableting Process

"Tableting" is performed by conventional methods. There are no particular restrictions as long as it is a method by which the shape of a tablet is obtained under at least the minimum pressure necessary to retain the shape of a tablet. This "tableting" can be performed using, for instance, an ordinary tableting machine, such as a single tableting machine or a rotary tableting machine, and the like, after adding the necessary additives, beginning with lubricant such as magnesium stearate, and the like, to the above-mentioned "composition." Moreover, the above-mentioned "composition" can also be made into tablets using an external-lubricating tableting machine. Tableting pressure of usually approximately 25 to approximately 800 kg/punch is preferred, approximately 50 to approximately 500 kg/punch is further preferred, approximately 50 to approximately 300 kg/punch is most preferred.

Process (d): Humidifying and Drying Process

When the saccharide that is the "binder for quick-disintegrating tablets in the buccal cavity" used in the granulation process becomes amorphous and there is a reduction in strength of the tablet obtained by the tableting process due to absorption of moisture, that is, when the "binder for quick-disintegrating tablets in the buccal cavity" used in the present invention is a saccharide of high moldability and maltose, sorbitol, or trehalose is used, it is preferred that the following process of humidifying and drying be used:

"Humidifying" is performed in combination with the drying process, which is the process that follows the humidifying process. There are no special restrictions to the method as long as it is one with which the saccharide of the "binder for quick-disintegrating tablets of the buccal cavity" used in the present invention crystallizes from amorphous substance. The conditions of this "humidifying" are determined from the apparent critical relative humidity of the mixture comprising sustained-release fine particle containing drug, "binder for quick-disintegrating tablets in the buccal cavity" used in the present invention, and "filler." Humidifying is usually performed to at least the critical relative humidity of this mixture. For instance, approximately 30 to approximately 100 RH % is preferred and approximately 50 to approximately 90 RH % is further preferred as the humidity. Approximately 15 to approximately 50° C. is preferred and approximately 20 to approximately 40° C. is further preferred as the temperature at this time. One to 48 hours is preferred and 12 to 24 hours is further preferred as the humidifying time.

There are no particular restrictions to the "drying" as long as it is a method by which the moisture that has been absorbed by humidifying is eliminated. Usually approximately 10 to approximately 100° C. is preferred, approximately 20 to approximately 60° C. is further preferred, and approximately 25 to approximately 40° C. is most preferred as the "drying" conditions. Thirty minutes to 10 hours is preferred and 1 to 4 hours is further preferred as the drying time.

Process (d'): Heating Process

The "heating" in the present invention is performed by conventional methods, and there are no special restrictions as long as it is a method whereby the molded article obtained by process (c) can be brought to a temperature that is at least the melting point of the above-mentioned "saccharide with a low melting point." Said "heating" process can be performed, for instance, using a ventilation oven. Temperature conditions are selected as needed depending on the type of "saccharide with a low melting point", and there are no particular restrictions as long as it is the melting point of the "saccharide with a low melting point" used in the present invention or higher and the melting point of the "saccharide with a high melting point" or lower. When the "saccharide with a low melting point" used in the present invention is used, it is approximately 80 to approximately 180° C., preferably approximately 90 to approximately 150° C. Time conditions are selected as needed depending on the type of saccharide that is used, the desired tablet strength, disintegration performance in the buccal cavity, and the like, but it is usually 0.5 to 120 minutes, preferably 1 to 60 minutes, further preferably 2 to 30 minutes.

Process (e): Cooling Process

The "cooling" in the present invention is performed by conventional methods, and there are no particular restrictions as long as it is a method whereby the saccharide with a low melting point that is used in the present invention is solidified after melting. Said "cooling" can be performed by, for instance, being set aside at room temperature or being stored in a low-temperature atmosphere, such as a refrigerator, and the like.

Next, an example of the method of manufacturing the composition comprising sustained-release fine particles for quick-disintegrating tablets in the buccal cavity of the present invention is given below: First, drug is layered and coated on commercial crystalline cellulose particles (for instance, Celphere 102) using an appropriate binder (for instance, hydroxypropylmethyl cellulose) with a fluidized bed granulator, and the like. Sustained-release fine particles are obtained by further coating a mixture of water-insoluble polymer substance (for instance, ethyl cellulose) and water-soluble polymer (for instance, hydroxypropylmethyl cellulose) as needed using a fluidized bed granulator, and the like, in order to obtain the desired dissolution. Then these fine particles and sugar (for instance, mannitol) are intermittently granulated (for instance, cycle of spraying for 10 seconds and then drying for 30 seconds) with the binder for quick-disintegrating tablets in the buccal cavity (for instance, maltose) using a fluidized bed granulator, and the like, to obtain the composition comprising sustained-release fine particles for quick-disintegrating tablets in the buccal cavity of the present invention.

Quick-disintegrating tablets in the buccal cavity comprising sustained-release fine particles can be prepared by adding additives as necessary, for example, an appropriate lubricant such as magnesium stearate, and the like, to the composition comprising sustained-release fine particles used for quick-disintegrating tablets in the buccal cavity of the present invention and making tablets using a tableting machine.

DETAILED DESCRIPTION OF THE INVENTION

Figure 1:
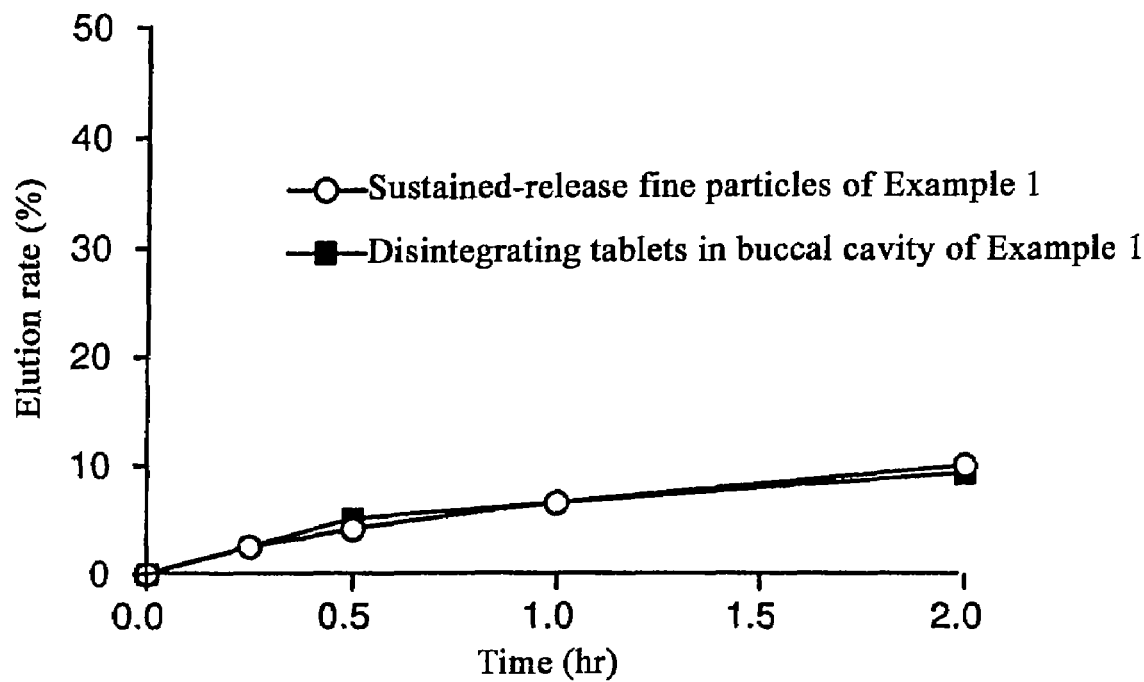
FIG. 1 is the results of dissolution experiments with Japan Pharmacopoeia 1st Fluid for Disintegration Tests of the tablets and sustained-release fine particles of Example 1.

The present invention will be further described below with examples, but interpretation of the present invention is not limited to these examples.

Methods of Evaluating Composition Comprising Sustained-Release Fine Particles

[Determination of Particle Diameter Distribution of Sustained-Release Fine Particles and Composition Comprising Sustained-Release Fine Particles]

Particle diameter was determined with a sieve-type particle diameter distribution gauge (Seishin Enterprise Co., Ltd. Robot Sifter) using sieves with openings of 30, 42, 60, 80, 100, 150, 200, and 250 mesh.

[Determination of Quantitative Ratio by Particle Diameter of Composition Comprising Sustained-Release Fine Particles]

Composition remaining on sieves with each of the above-mentioned opening sizes is recovered and the quantitative amount of each fraction is determined. Assuming that the total quantitative amount is 100%, the ratio accounted for by the quantitative amount on each sieve is calculated and serves as the quantitative ratio by particle diameter. Moreover, the quantitative distribution by particle diameter was obtained by arranging the quantitative ratio by particle diameter in the order of the opening size of each sieve. Incidentally, any method can be used to determine the quantitative amount as long as the drug that is contained is thoroughly recovered from the composition, and determination is performed by the determination method suitable for each drug.

[Ratio of Ungranulated Sustained-Release Fine Particles]

The particle diameter distribution of sustained-release fine particles and the quantitative distribution by particle diameter of the composition comprising sustained-release fine particles is determined and calculated by the following formula:

Ratio of ungranulated sustained release fine particles $(\%) = G_1 + \Sigma(G_{i+1} - (P_i - G_i))$ Here, the estimation of $\Sigma$ is obtained by calculation from $i=1$ and estimating the value up to the point before $(G_{i+1} - (P_i - G_i))$ becomes negative.

$P_1$: sustained-release fine particle ratio on sieve with smallest opening size within the particle diameter distribution of the sustained-release fine particles (with the exception of that where it is 0%). That is, it is 15.0% on 150 mesh in the following examples.

$P_2$: sustained-release fine particle ratio on sieve with second smallest opening size within particle diameter distribution of sustained-release fine particles (with the exception of that where it is 0%). That is, it is 70.6% on 100 mesh in the following examples. The third, fourth and so on is referred to as $P_3$, $P_4$ and they are as a whole represented as $P_i$.

$G_1$: value of quantitative ratio by particle diameter distribution of composition on sieve with the same opening size as $P_1$. That is, it is 2.5% on 150 mesh in the following examples.

$G_2$: value of quantitative ratio by particle diameter distribution of composition on sieve with same opening size as $P_2$. That is, it is 14.3% on 100 mesh in the following examples. The third, fourth, and so on are referred to as $G_3$, $G_4$, and so on, and they are as a whole represented as $G_i$.

For instance, if the determination results are as follows:

| | Particle diameter distribution of sustained-release fine particles | Quantitative distribution by particle diameter of Example 1 composition |
|---|---|---|
| 30 Mesh on (%) | 0 | 19.0 |
| 42 Mesh on (%) | 0 | 22.4 |
| 60 Mesh on (%) | 0 | 23.5 |
| 80 Mesh on (%) | 14.4 | 18.2 |
| 100 Mesh on (%) | 70.6 | 14.3 |
| 150 Mesh on (%) | 15.0 | 2.5 |
| 200 Mesh on (%) | 0 | 0 |
| 200 Mesh pass (%) | 0 | 0 | the ratio (%) of ungranulated sustained-release fine particles $$= G_1 + \Sigma(G_{i+1} - (P_i - G_i))$$
$$= G_1 + (G_2 - (P_1 - G_1)) + (G_3 - (P_2 - G_2)) + \ldots$$
$$= 2.5 + (14.3 - (15 - 2.5)) + (18.2 - (70.6 - 14.3)) + (23.5 - (14.4 - 18.2))$$
$$= 2.5 + (+1.8) + (-38.1)$$

If the figures in parentheses are negative, it means that the sustained-release fine particles have a particle diameter that is at least 1 rank larger because of granulation. Therefore, there is no further estimation performed and $$= 2.5 + (+1.8)$$
$$= 4.3$$

Methods for Evaluating Quick-Disintegrating Tablets in the Buccal Cavity

[Hardness tests] Determinations were performed using a Schleuniger tablet hardness meter (Schleuniger Co., Ltd.). The tests were performed with 5 tablets and the mean is shown. Tablet hardness is represented by the force needed to crush the tablet (units kp). A larger number indicates a stronger tablet.

[Friability] Determinations were performed using a friability tester (model PTFR-A, Pharma Test Co.) The friability is found using 6 g tablets. It is represented by the percentage weight loss of a tablet after being turned 100 times at a turning speed of 25 rpm. A smaller value indicates a stronger tablet surface.

[Disintegration in buccal cavity tests] Healthy adult males placed the tablet of the present invention in their buccal cavity without any water in the buccal cavity and the time until the tablet was completely disintegrated and dissolved by saliva only was determined.

[Content uniformity tests] The drug content of each of 10 tablets was quantitatively determined and is represented as the coefficient of variation (CV %) of the amount of drug from the above-mentioned formula.

[Dissolution tests] Tests were conducted by Dissolution Test Method No. 2 in accordance with Revised Version 12 of the Japanese Pharmacopoeia.

Example 1

Eighty grams tamsulosin hydrochloride and 80 g hydroxypropylmethyl cellulose (TC5E, Shin-Etsu Chemical Co., Ltd.) were dissolved in a mixture of 304 g purified water and 2,736 g methanol. Four-thousand grams Celphere 102 (brand name, Asahi Kasei, mean particle diameter of approximately 127 μm, particle diameter of approximately 50 to approximately 150 μm) were introduced to a fluidized bed granulator (Freund Industries, FLO-5) and coated with this solution by the side spraying method (spraying liquid volume 100 g/min, spraying air pressure 4 kg/cm$^2$, product temperature 40° C., inlet temperature 80° C.) to obtain tamsulosin hydrochloride particles. Separately, 533 g ethyl cellulose (Nissin Chemistry Co.) and 187 g hydroxypropylmethyl cellulose (TC5E, brand name, Shin-Etsu Chemical Co., Ltd.) were dissolved in a mixture of 698 g purified water and 22,582 g methanol. Four thousand grams tamsulosin hydrochloride particles were introduced to a fluidized bed granulator (Freund Industries, FLO-5) and coated with this solution by side spraying (spraying liquid volume of 40 g/min, spraying air pressure of 4 kg/cm$^2$, product temperature of 50° C., inlet temperature of 60° C.) to obtain sustained-release fine particles. Four-thousand grams of these sustained-release fine particles were introduced to a fluidized bed granulator (Freund Industries, FLO-5) and coated with a mixture of 2,000 g Aquacoat (brand name, Asahi Kasei), 4,000 g Eudragit L30D55 (brand name, Röhm), 667 g Eudragit NE30D (brand name, Röhm), and 6,667 g purified water (spraying liquid volume of 40 g/min, spraying air pressure of 4 kg/cm$^2$, product temperature of 40° C., inlet temperature of 60° C.) to obtain enteric sustained-release fine particles.

Then 368 g of these enteric sustained-release fine particles, 2,560 g mannitol (Towa Kasei Co., Ltd.), and 640 g lactose (Domomilk) were granulated (spraying liquid volume 200 g/min, spraying air pressure of 1.5 kg/cm$^2$, product temperature of 29° C., inlet temperature of 80° C., spraying cycle of 10 seconds spraying to 30 seconds drying) with an aqueous 40% w/w solution containing 400 g maltose (Hayashibara Co., Ltd., brand name: Sunmalt S) in a fluidized bed granulator (Freund Industries, FLO-5) to obtain the composition of the present invention.

After further mixing 32 g calcium stearate with the composition that was obtained, 200 mg tablets containing 0.2 mg tamsulosin hydrochloride per tablet were made under a tableting pressure of 100 kg/punch and an initial hardness of 1.0 kp using a rotary tableting machine. Next, these tablets were kept for 18 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 5.9 kp (n=5), friability of 0.8% (100 rounds) and disintegration time in the buccal cavity of 20 seconds (n=3). Moreover, as a result of evaluating uniformity of content, CV %=2.1%, proving that there is good uniformity of content.

Comparative Example 1

First, 319.3 g mannitol (Towa Kasei Co., Ltd) and 79.7 g lactose (Domomilk) were granulated (spraying liquid volume 10 g/min, spraying air pressure 1.5 kg/cm$^2$, product temperature 30° C., inlet temperature 60° C., spraying cycle: continuous spraying) with an aqueous 20% w/w solution containing 50 g maltose (Hayashibara Co., Ltd., brand name: Sunmalt S) in a fluidized bed granulator (Freund Industries, uni-glatt). After mixing 45.2 g of the enteric sustained-release fine particles prepared in Example 1 and 5 g calcium stearate with the product that was obtained, 200 mg tablets containing 0.2 mg tamsulosin hydrochloride per tablet were made under a tableting pressure of 93 kg/punch and an initial hardness of 1.0 kp using a rotary tableting machine. Next, these tablets were kept for 18 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained had a hardness of 4.1 kp (n=5) and a disintegration time in the buccal cavity of 15 seconds (n=3). Moreover, the results of evaluating uniformity of content were CV %=5.6%, with the tablets having inferior uniformity of content.

Comparative Example 2

First, 45.2 g enteric sustained-release fine particles prepared in Example 1, 319.3 g mannitol (Towa Kasei Co., Ltd.), and 79.7 g lactose (Domomilk) were granulated (spraying liquid volume 10 g/min, spraying air pressure 1.5 kg/cm$^2$, product temperature 30° C., inlet temperature 60° C., spraying cycle: continuous spraying) with an aqueous 20% w/w solution containing 50 g maltose (Hayashibara Co., Ltd., brand name: Sunmalt S) in a fluidized bed granulator (Freund Industries, uni-glatt). After mixing 5 g calcium stearate with the product that was obtained, 200 mg tablets containing 0.2 mg tamsulosin hydrochloride per tablet were made under a tableting pressure of 96 kg/punch and an initial hardness of 1.0 kp using a rotary tableting machine. Next, these tablets were kept for 18 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained had a hardness of 3.7 kp (n=5) and a disintegration time in the buccal cavity of 15 seconds (n=3). Moreover, the results of evaluating uniformity of content were CV %=4.0%, with the tablets having inferior uniformity of content.

Experiment 1 (Quantitative Amount by Particle Diameter Distribution)

The particle diameter distribution of the sustained-release fine particles obtained in Example 1 and the particle diameter distribution as well as quantitative distribution by particle diameter of the composition prepared in Examples 1 and 2 (Table 1) as well as the product prepared in Comparative Examples 1 and 2 (Table 2) are shown together.

Table 1. Particle diameter distribution of sustained release fine particles and particle diameter distribution and quantitative distribution by particle diameter of compositions of Examples 1 and 2

TABLE 1

Particle diameter distribution of sustained release fine particles and particle diameter distribution and quantitative distribution by particle diameter of compositions of Examples 1 and 2

|  | Particle diameter distribution of sustained-release fine particles | Particle diameter distribution of Example 1 composition | Quantitative distribution by particle diameter of Example 1 composition | Particle diameter distribution of Example 2 composition | Quantitative distribution by particle diameter of Example 2 composition |
|---|---|---|---|---|---|
| Mean particle diameter (μm) | 165 | 393 | — | 204 | — |
| 30 Mesh on (%) | 0 | 26.9 | 19.0 | 1.5 | 1.1 |
| 42 Mesh on (%) | 0 | 29.7 | 22.4 | 5.1 | 6.2 |
| 60 Mesh on (%) | 0 | 23.8 | 23.5 | 23.1 | 27.2 |
| 80 Mesh on (%) | 14.4 | 9.8 | 18.2 | 31.5 | 43.4 |
| 100 Mesh on (%) | 70.6 | 2.8 | 14.3 | 15.2 | 17.6 |
| 150 Mesh on (%) | 15.0 | 3.1 | 2.5 | 16.1 | 4.3 |
| 200 Mesh on (%) | 0 | 1.5 | 0 | 5.1 | 0 |
| 200 Mesh pass (%) | 0 | 2.5 | 0 | 2.5 | 0 |
| Ratio of ungranulated product (%) | — | — | 4.3 | — | 11.2 |

Table 2. Particle diameter distribution of sustained-release fine particles and particle diameter distribution as well as quantitative distribution by particle diameter of products in Comparative Examples 1 and 2

TABLE 2

Particle diameter distribution of sustained-release fine particles and particle diameter distribution as well as quantitative distribution by particle diameter of products in Comparative Examples 1 and 2

|  | Particle diameter distribution of sustained-release fine particles | Particle diameter distribution of Comparative Example 1 product | Quantitative distribution by particle diameter of Comparative Example 1 product | Particle diameter distribution of Comparative Example 2 product | Quantitative distribution by particle diameter of Comparative Example 2 product |
|---|---|---|---|---|---|
| Mean particle diameter (μm) | 165 | 179 | — | 196 | — |
| 30 Mesh on (%) | 0 | 4.7 | 0 | 3.1 | 2.1 |
| 42 Mesh on (%) | 0 | 8.0 | 0 | 11.3 | 10.3 |
| 60 Mesh on (%) | 0 | 13.8 | 0 | 17.8 | 19.3 |
| 80 Mesh on (%) | 14.4 | 23.6 | 14.2 | 23.4 | 42.2 |
| 100 Mesh on (%) | 70.6 | 18.9 | 70.9 | 12.8 | 21.2 |
| 150 Mesh on (%) | 15.0 | 17.8 | 14.4 | 13.8 | 4.9 |
| 200 Mesh on (%) | 0 | 8.4 | 0 | 8.8 | 0 |
| 200 Mesh pass (%) | 0 | 4.9 | 0 | 9.0 | 0 |
| Ratio of ungranulated product (%) | — | — | 99.2 | — | 16.0 |

The majority of sustained-release fine particles are within 80 to 100 mesh and the results of quantitative ratio by particle diameter distribution in Examples 1 and 2 confirm that most of the sustained-release fine particles are coated with filler by granulation and distribution of composition comprising sustained-release fine particles shifts in the direction of a large particle diameter. On the other hand, with respect to distribution of the product in Comparative Example 2, it is confirmed that apparent particle diameter is large, but the quantitative ratio by particle diameter does not necessarily coincide with distribution of the product. In particular, the quantitative ratio for 80 to 100 mesh, under which the ungranulated sustained-release particles fall, is 20% or higher and it was observed there are many sustained-release particles that are not granulated.

Separately, many sustained-release fine particles that were not granulated were observed in the 80-150 mesh part of the product of Comparative Example 2 as a result of microscopic observation of composition and product. On the other hand, almost no ungranulated sustained-release fine particles were observed with the composition of Example 1. Thus, finding that support the above-mentioned data were obtained even by microscopic observation. Consequently, these results confirm that the sustained-release fine particles were thoroughly granulated by filler in the compositions of Examples 1 and 2. Moreover, the coefficient of variation when the ratio of ungranulated product was 4.3% (Example 1) and 11.2% (Example 2) was 2.2 (CV %) and 2.1 (CV %), respectively, while the coefficient of variation when the ratio of ungranulated product was 99.2% (Comparative Example 1) and 16.0% (Comparative Example 2) was 5.6 (CV %) and 4.0 (CV %), respectively. Therefore, if the ratio of ungranulated product is 16% or higher, the results indicate that the coefficient of variation (CV %), which is an indicator of uniformity of content, is large and exceeds the allowable value of 3.5%.

Experiment 2 (Dissolution Experiment)

Dissolution experiments were performed on the tablets obtained in Example 1 and Comparative Examples 1 and 2 and the results were compared with the dissolution speed of sustained-release fine particles only. The experimental conditions were 100 rpm by the paddle method, and 500 ml each of Japanese Pharmacopoeia Disintegration Test Method $1^{st}$ fluid (pH 1.2) and $2^{nd}$ fluid (pH 6.8) were used as the experimental fluids.

Figure 2:
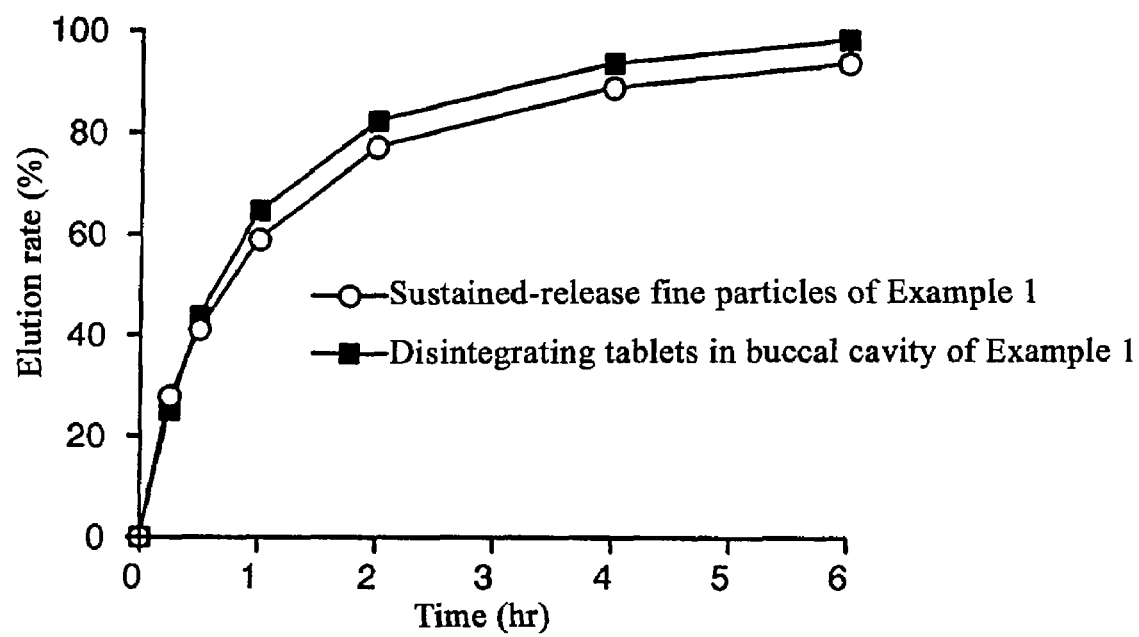
FIG. 2 is the results of dissolution experiments with Japan Pharmacopoeia 2nd Fluid for Disintegration Tests of the tablets and sustained-release fine particles of Example 1.
Figure 3:
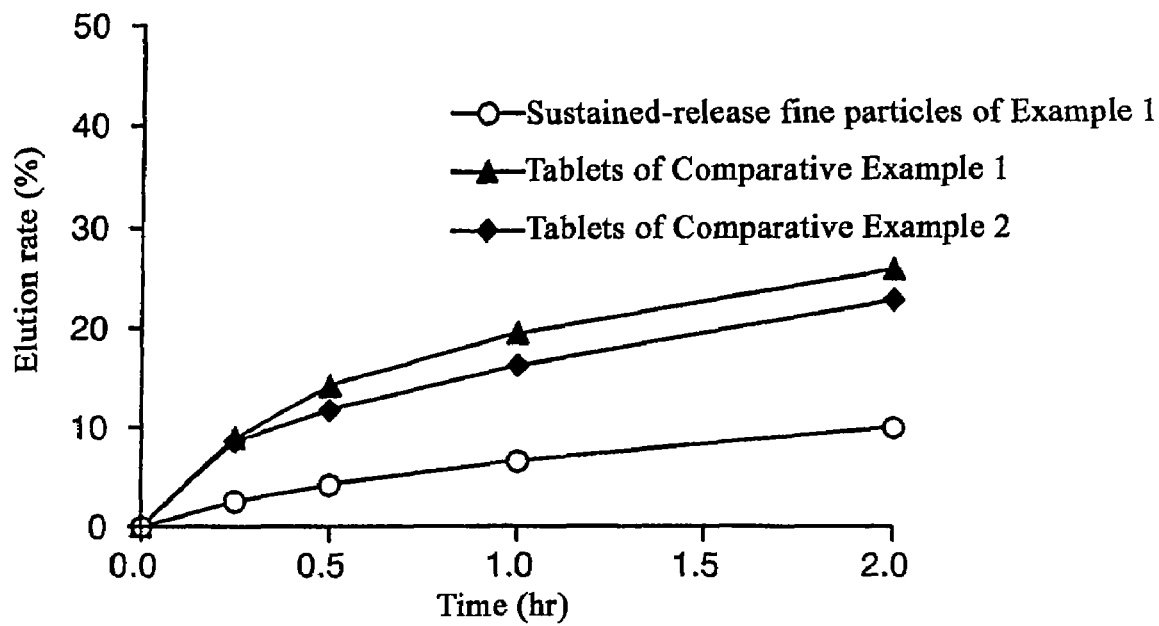
FIG. 3 is the results of dissolution experiments with Japan Pharmacopoeia 1st Fluid for Disintegration Tests of the tablets and sustained-release fine particles of Comparative Examples 1 and 2.

As a result of the experiment, in the Example there was almost no difference (difference in values after two hours of 0.7%) between the dissolution rate of the sustained-release fine particles and tablets up to two hours after starting the dissolution experiment with the test fluid having a pH of 1.2, and even with the test fluid having a pH of 6.8, the difference between the dissolution rate of the sustained-release fine particles and tablet was always less than 15% at 2.9%, 5.8%, and 5.1% at each dissolution time where the dissolution rate of sustained-release fine particles was 30%, 50%, and 80%, respectively, confirming that dissolution when tablets are made is not accelerated (FIGS. 1 and 2). On the other hand, acceleration of the dissolution speed when tablets were made was seen when compared to the sustained-release fine particles in the Comparative Examples (FIG. 3, difference between values after two hours of 15.9% and 12.8%). It was concluded that this was because in contrast to the fact that sustained-release fine particles were not confirmed on the tablet surface in Example 1, sustained-release fine particles were observed on the tablet surface in Comparative Examples 1 and 2 and therefore, the sustained-release fine particles had been destroyed as a result of contact between the punch surface and sustained-release fine particles.

Consequently, it was confirmed that by means of the present invention, sustained-release fine particles are thoroughly granulated by filler and acceleration of dissolution at the time tablets are made can be avoided.

Example 2

First, 2,609 g mannitol (Towa Kasei Co., Ltd.) and 653 g lactose (Domomilk) were pulverized with a pin mill pulverizing device (Hosokawa Micron). This pulverized product and 307 g enteric sustained-release fine particles prepared in Example 1 were granulated (spraying liquid volume 100 g/min, spraying air pressure 1.5 kg/cm², product temperature 28° C., inlet temperature 80° C., spraying cycles 20 seconds spraying-30 seconds drying) with an aqueous 20% w/w solution containing 400 g maltose (Hayashibara Co., Ltd., brand name: Sunmalt S) in a fluidized bed granulator (Freund Industries, FLO-5) to obtain the composition of the present invention. After mixing 32 g calcium stearate with this composition that was obtained, 120 mg tablets containing 0.1 mg tamsulosin hydrochloride per tablet were made under a tableting pressure of 100 kg/punch and initial hardness of 1.0 kp using a rotary tableting machine. Next, these tablets were stored for 18 hours while heating and humidifying at 25° C./70% RH using a thermostatic chamber at constant humidity (Tabaiespec Co., Ltd., PR-35C). Then they were dried for 3 hours at 30° C. and 40% RH. The tablets that were obtained had a hardness of 5.2 kp (n=5), friability of 0.6% (100 rounds), and a disintegration time in the buccal cavity of 20 seconds (n=3). Moreover, the results of evaluating uniformity of content were CV %=2.2%, confirming that the tablets have good uniformity of content. Furthermore, as a result of performing dissolution tests on the sustained-release fine particles and the tablets that were obtained, it was confirmed that the difference in the dissolution rate between the sustained-release fine particles and tablet was 4.7% up to two hours after starting the dissolution test with the test fluid having a pH of 1.2, and even with the test fluid having a pH of 6.8, the difference in the dissolution rate between the sustained-release fine particles and tablet was always less than 15% at 2.3%, 2.4%, and 1.4% at each dissolution time where the dissolution rate of sustained release fine particles was 30%, 50%, and 80%, respectively, indicating that dissolution at the time of tableting is not accelerated.

Tablets were separately made with the same composition and by the same manufacturing method as previously described. The tablets that were obtained had a hardness of 5.6 kp (n=5), friability of 0.6% (100 rounds), and dissolution time in the buccal cavity of 25 seconds (n=3). Moreover, the results of evaluating uniformity of content showed CV %=2.5%. As with the above-mentioned findings, the results of dissolution tests did not reveal the difference between the dissolution rates of the sustained-release fine particles and the tablet. Thus, by means of the present invention, a composition comprising sustained-release fine particles is prepared and therefore, uniformity of content is guaranteed as a result of preventing segregation between the sustained-release fine particles and filler. In addition, it was confirmed that reproducibility is obtained.

Example 3

Three-hundred grams acetaminophen (Yoshitomi Fine Chemicals Co., Ltd.) and 60 g hydroxypropylmethyl cellulose (TC5E, Shin-Etsu Chemical Co., Ltd.) were dissolved in a mixture of 720 g methanol and 720 g dichloromethane. Three-hundred grams Celphere 102 (brand name, Asahi Kasei, mean particle diameter of approximately 127 μm, particle diameter of approximately 50 to approximately 150 μm) were introduced to a fluidized bed granulator (Freund Industries, uni-glatt) and coated with the solution by the side spraying method (spraying liquid volume 14 g/min, spraying air pressure 3 kg/cm², product temperature 32° C., inlet temperature 45° C.) to obtain acetaminophen particles. Separately, 48 g ethyl cellulose (Nissin Chemistry Co.) and 12 g hydroxypropylmethyl cellulose (TC5E, brand name, Shin-Etsu Chemical Co., Ltd.) were dissolved in a mixture of 57 g purified water and 1,083 g methanol. Three-hundred grams acetaminophen particles were introduced to a fluidized bed granulator (Freund Industries, uni-glatt) and coated with this solution by side spraying (spraying liquid volume of 8 g/min, spraying air pressure of 3 kg/cm², product temperature of 38° C., inlet temperature of 67° C.) to obtain sustained-release fine particles. Sixty-six grams of these sustained-release fine particles and 314.25 g mannitol (Towa Kasei Co., Ltd) that had been pulverized by a pin mill pulverizing device (Hosokawa Micron) were granulated (spraying liquid volume 15 g/min, spraying air pressure of 1.1 kg/cm², product temperature of 30° C., inlet temperature of 38° C., spraying cycle of 30 seconds spraying-30 seconds drying) with an aqueous 30% w/w solution containing 67.5 g maltose (Hayashibara Co., Ltd., brand name: Sunmalt S) in a fluidized bed granulator (Freund Industries, uni-glatt) to obtain the composition of the present invention. The ratio of ungranulated sustained-release fine particles was 0.0%. After further mixing 2.25 g magnesium stearate with the composition that was obtained, 450 mg tablets containing 25 mg acetaminophen per tablet were made under a tableting pressure of 25 kg/punch and an initial hardness of 2.0 kp using a rotary tableting machine. Next, these tablets were kept for 24 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 3.5 kp (n=5) and disintegration time in the buccal cavity of 12 seconds (n=1). Moreover, as a result of evaluating uniformity of content, CV %=1.2%, confirming that there is good uniformity of content. Furthermore, when dissolution of the sustained-release fine particles and tablet was compared 2.8 hours after starting dissolution tests (time when there is approximately 30% dissolution of sustained-release fine particles), 5 hours after (time when there is approximately 50% dissolution of sustained-release fine particles), and 9 hours after (time when there is approximately 80% dissolution of sustained-release fine particles) and the difference was calculated, it was 4.9% at 2.8 hours, 4.6% at 5 hours, and 2.5% at 9 hours, confirming that acceleration of dissolution of sustained-release fine particles is prevented at any time.

Example 4

Six-hundred grams acetaminophen (Yoshitomi Fine Chemical Co., Ltd.) and 120 g hydroxypropylmethyl cellulose (TC5E, Shin-Etsu Chemical Co., Ltd.) were dissolved in a mixture of 1,440 g methanol and 1,440 g dichloromethane. Three-hundred grams sodium chloride (Shin Nihon Salt Co., Ltd., EF-70 classification, mean particle diameter of approximately 67 μm, particle diameter of approximately 75 μm or smaller) were introduced to a fluidized bed granulator (Freund Industries, uni-glatt) and coated with this solution by the side spraying method (spraying liquid volume 10 g/min, spraying air pressure 3 kg/cm², product temperature 33° C., inlet temperature 55° C.) to obtain acetaminophen particles.

Separately, 72 g ethyl cellulose (Nissin Chemistry Co.) and 8 g hydroxypropylmethyl cellulose (TC5E, brand name, Shin-Etsu Chemical Co., Ltd.) were dissolved in a mixture of 76 g purified water and 1,444 g methanol. Four-hundred grams acetaminophen particles were introduced to a fluidized bed granulator (Freund Industries, uni-glatt) and coated with this solution by side spraying (spraying liquid volume of 10 g/min, spraying air pressure of 3 kg/cm², product temperature of 39° C., inlet temperature of 70° C.) to obtain sustained-release fine particles.

Then 76.5 g of these sustained-release fine particles and 393.4 g mannitol (Towa Kasei Co., Ltd) that had been pulverized by a pin mill pulverizing device (Hosokawa Micron) were granulated (spraying liquid volume 15 g/min, spraying air pressure of 1.0 kg/cm², product temperature of 29° C., inlet temperature of 35° C., spraying cycle of 20 seconds spraying-40 seconds drying) with an aqueous 20% w/w solution containing 52.5 g maltose (Hayashibara Co., Ltd., brand name: Sunmalt S) in a fluidized bed granulator (Freund Industries, uni-glatt) to obtain the composition of the present invention. The ratio of ungranulated sustained-release fine particles was 10.8%.

After further mixing 2.6 g magnesium stearate with the composition that was obtained, 350 mg tablets containing 25 mg acetaminophen per tablet were made under a tableting pressure of 50 kg/punch and an initial hardness of 1.9 kp using a rotary tableting machine. Next, these tablets were kept for 24 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 4.8 kp (n=5), friability of 1.23% (100 rounds), and disintegration time in the buccal cavity of 13 seconds (n=1). Moreover, as a result of evaluating uniformity of content, CV %=2.4%, confirming that there is good uniformity of content. Furthermore, when dissolution of the sustained-release fine particles and tablet was compared 2.8 hours after starting dissolution tests (time when there is approximately 30% dissolution of sustained-release fine particles), 5 hours after (time when there is approximately 50% dissolution of sustained-release fine particles), and 9.5 hours after (time when there is approximately 80% dissolution of sustained-release fine particles) and the difference was calculated, it was 5.5% at 2.8 hours, 3.5% sustained-release fine particles [sic] at 5 hours, and 3.1% at 9.5 hours, confirming that acceleration of dissolution of sustained-release fine particles is prevented at any time.

Example 5

First, 1,200 g acetaminophen and 120 g hydroxypropylmethyl cellulose (TC5E, Shin-Etsu Chemical Co., Ltd.) were dissolved in a mixture of 2,640 g methanol and 2,640 g dichloromethane. Three-hundred grams sodium chloride (Shin Nihon Salt Co., Ltd., EF-70 classification, mean particle diameter of approximately 67 μm, particle diameter of 75 μm or smaller) were introduced to a fluidized bed granulator (Freund Industries, uni-glatt) and coated with this solution by the side spraying method (spraying liquid volume 16 g/min, spraying air pressure 3 kg/cm², product temperature 30° C., inlet temperature 75° C.) to obtain acetaminophen particles.

Separately, 45.9 g ethyl cellulose (Nissin Chemistry Co.) and 5.1 g hydroxypropylmethyl cellulose (TC5E, brand name, Shin-Etsu Chemical Co., Ltd.) were dissolved in a mixture of 48.5 g purified water and 920.5 g methanol. Three-hundred forty grams acetaminophen particles were introduced to a fluidized bed granulator (Freund Industries, uni-glatt) and coated with this solution by side spraying (spraying liquid volume of 8 g/min, spraying air pressure of 2.5 kg/cm², product temperature of 39° C., inlet temperature of 75° C.) to obtain sustained-release fine particles. Then 116.4 g of these sustained-release fine particles and 542.7 g mannitol (Towa Kasei Co., Ltd) that had been pulverized by a pin mill pulverizing device (Hosokawa Micron) were granulated (spraying liquid volume 15 g/min, spraying air pressure of 1.1 kg/cm², product temperature of 28° C., inlet temperature of 35° C., spraying cycle of 20 seconds spraying-40 seconds drying) with an aqueous 30% w/w solution containing 117 g maltose (Hayashibara Co., Ltd., brand name: Sunmalt S) in a fluidized bed granulator (Freund Industries, uni-glatt) to obtain the composition of the present invention. The ratio of ungranulated sustained-release fine particles was 1.6%.

After further mixing 3.9 g magnesium stearate with the composition that was obtained, 520 mg tablets containing 50 mg acetaminophen per tablet were made under a tableting pressure of 200 kg/punch and an initial hardness of 1.9 kp using a rotary tableting machine. Next, these tablets were kept for 24 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 6.4 kp (n=5), friability of 1.13% (100 rounds), and disintegration time in the buccal cavity of 21 seconds (n=1). Moreover, as a result of evaluating uniformity of content, CV %=3.3%, confirming that there is good uniformity of content. Furthermore, when dissolution of the sustained-release fine particles and tablet was compared 2.5 hours after starting dissolution tests (time when there is approximately 30% dissolution of sustained-release fine particles), 5 hours after (time when there is approximately 50% dissolution of sustained-release fine particles), and 9.5 hours after (time when there is approximately 80% dissolution of sustained-release fine particles) and the difference was calculated, it was 8.8% at 2.5 hours, 6.3% at 5 hours, and 3.3% at 9.5 hours, confirming that acceleration of dissolution of sustained-release fine particles is prevented at any time.

Example 6

Forty grams ethyl cellulose (Nissin Chemistry Co.) were dissolved in a mixture of 380 g methanol and 380 g dichloromethane. Four-hundred grams sodium chloride (Shin Nihon Salt Co., Ltd., EF-70 classification, mean particle diameter of approximately 67 μm, particle diameter of 75 μm or smaller) were introduced to a fluidized bed granulator (Freund Industries, uni-glatt) and coated with this solution by the side spraying method (spraying liquid volume 6 g/min, spraying air pressure 2 kg/cm², product temperature 28° C., inlet temperature 60° C.) to obtain core particles. Then 1,200 g acetaminophen (Yoshitomi Fine Chemicals Co., Ltd.) and 120 g hydroxypropylmethyl cellulose (TC5E, Shin-Etsu Kagaku Co., Ltd.) were dissolved in a mixture of 2,640 g methanol and 2,640 g dichloromethane. Three-hundred grams of the above-mentioned core particles were introduced to a fluidized bed granulator (Freund Industries, uni-glatt) and coated with this solution by the side spraying method (spraying liquid volume 15 g/min, spraying air pressure 3 kg/cm², product temperature 30° C., inlet temperature 70° C.) to obtain acetaminophen particles.

Separately, 47.2 g ethyl cellulose (Nissin Chemistry Co.) and 5.3 g hydroxypropylmethyl cellulose (TC5E, brand name, Shin-Etsu Chemical Co., Ltd.) were dissolved in a mixture of 49.9 g purified water and 947.6 g methanol. Three-hundred fifty grams acetaminophen particles were introduced to a fluidized bed granulator (Freund Industries, uni-glatt) and coated with this solution by side spraying (spraying liquid volume of 8 g/min, spraying air pressure of 2.5 kg/cm², product temperature of 37° C., inlet temperature of 75° C.) to obtain sustained-release fine particles. Then 116.4 g of these sustained-release fine particles and 542.7 g mannitol (Towa Kasei Co., Ltd) that had been pulverized by a pin mill pulverizing device (Hosokawa Micron Co., Ltd.) were granulated (spraying liquid volume 15 g/min, spraying air pressure of 1.1 kg/cm$^2$, product temperature of 30° C., inlet temperature of 40° C., spraying cycle of 20 seconds spraying-40 seconds drying) with an aqueous 30% w/w solution containing 117 g maltose (Hayashibara Co., Ltd., brand name: Sunmalt S) in a fluidized bed granulator (Freund Industries, uni-glatt) to obtain the composition of the present invention. The ratio of ungranulated sustained-release fine particles was 3.9%.

After further mixing 3.9 g magnesium stearate with the composition that was obtained, 520 mg tablets containing 50 mg acetaminophen per tablet were made under a tableting pressure of 140 kg/punch and an initial hardness of 2.6 kp using a rotary tableting machine. Next, these tablets were kept for 24 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 5.9 kp (n=5), friability of 1.64% (100 rounds), and disintegration time in the buccal cavity of 26 seconds (n=1). Moreover, as a result of evaluating uniformity of content, CV %=2.0%, confirming that there is good uniformity of content. Furthermore, when dissolution of the sustained-release fine particles and tablet was compared 2.3 hours after starting dissolution tests (time when there is approximately 30% dissolution of sustained-release fine particles), 5.5 hours after (time when there is approximately 50% dissolution of sustained-release fine particles), and 13.5 hours after (time when there is approximately 80% dissolution of sustained-release fine particles) and the difference was calculated, it was 0.6% at 2.3 hours, 1.2% at 5.5 hours, and 3.2% at 13.5 hours, confirming that acceleration of dissolution of sustained-release fine particles is prevented at any time.

Example 7

Eighty grams tamsulosin hydrochloride and 80 g hydroxypropyl[methyl] cellulose (TC5E, Shin-Etsu Chemical Co., Ltd.) were dissolved in a mixture of 304 g purified water and 2,736 g methanol. Four-thousand grams Celphere 102 (brand name, Asahi Kasei, mean particle diameter of approximately 127 μm, particle diameter of approximately 50 to approximately 150 μm) were introduced to a fluidized bed granulator (Freund Industries, FLO-5) and coated with this solution by the side spraying method (spraying liquid volume 100 g/min, spraying air pressure 4 kg/cm$^2$, product temperature 40° C., inlet temperature 80° C.) to obtain tamsulosin hydrochloride particles.

Separately, 43.7 g ethyl cellulose (Nissin Chemistry Co.) and 12.3 g hydroxypropylmethyl cellulose (TC5E, brand name, Shin-Etsu Chemical Co., Ltd.) were dissolved in a mixture of 43.9 g purified water and 833.4 g methanol. Four-hundred grams tamsulosin hydrochloride particles were introduced to a fluidized bed granulator (Freund Industries, uni-glatt) and coated with this solution by side spraying (spraying liquid volume of 6 g/min, spraying air pressure of 4 kg/cm$^2$, product temperature of 40° C., inlet temperature of 63° C.) to obtain sustained-release fine particles.

Next, 300 g of these sustained-release fine particles were introduced to a fluidized bed granulator (Freund Industries, uni-glatt) and coated with a mixture of 90 g Aquacoat (brand name, Asahi Kasei), 180 g Eudragit L30D55 (brand name, Röhm), 30 g Eudragit NE30D (brand name, Röhm), and 300 g purified water (spraying liquid volume of 6 g/min, spraying air pressure of 3 kg/cm$^2$, product temperature of 40° C., inlet temperature of 75.5° C.) to obtain enteric sustained-release fine particles. Then 92.5 g of these enteric sustained-release fine particles, 568.2 g mannitol (Towa Kasei Co., Ltd.) and 142.1 g lactose (Domomilk) that had been pulverized with a pin mill pulverizing device (Hosokawa Co., Ltd.), and 72 g erythritol (Nikken Chemicals Co., Ltd.) were granulated (spraying liquid volume 15 g/min, spraying air pressure of 0.5 kg/cm$^2$, product temperature of 40° C., inlet temperature of 70° C., spraying cycle of 15 seconds spraying-30 seconds drying) with an aqueous 5% w/w solution containing 18 g copolyvidone (BASF Co., brand name Kollidon VA64) in a fluidized bed granulator (Freund Industries, uni-glatt) to obtain the composition of the present invention. The ratio of ungranulated fine particles was 3.0%.

After further mixing 7.2 g calcium stearate with the composition that was obtained, 300 mg tablets containing 0.4 mg tamsulosin hydrochloride per tablet were made under an initial hardness of 0.6 kp using a rotary tableting machine. Next, these tablets were heated for 13 minutes at 120° C. using a program oven (model No. MOV-112P, Sanyo Corporation) and then cooled at room temperature for 30 minutes. The tablets that were obtained showed a hardness of 6.8 kp (n=5), friability of 0.28% (100 rounds) and disintegration time in the buccal cavity of 27 seconds (n=1). Moreover, as a result of evaluating uniformity of content, CV %=1.6%, proving that there is good uniformity of content. Furthermore, when dissolution of the sustained-release fine particles and tablet was compared 1 hour after starting dissolution tests (time when there is approximately 30% dissolution of sustained-release fine particles), 2 hours after (time when there is approximately 50% dissolution of sustained-release fine particles), and 6 hours after (time when there is approximately 80% dissolution of sustained-release fine particles) and the difference was calculated, it was 1.1% at 1 hour, 2.8% at 5 [sic] hours, and 9.4% at 6 hours, confirming that acceleration of dissolution of sustained-release fine particles is prevented at any time.

Example 8

First, 1,200 g nicardipine hydrochloride and 1,200 g hydroxypropylmethyl cellulose (TC5E, Shin-Etsu Chemical Co., Ltd.) were dissolved in a mixture of 4,800 g methanol and 4,800 g dichloromethane. Three-hundred grams silicon dioxide (Silica Gel, Sigma, mean particle diameter of approximately 48 μm, particle diameter of 75 μm or smaller) were introduced to a fluidized bed granulator (Freund Industries, uni-glatt) and coated with this solution by the side spraying method (spraying liquid volume 18 g/min, spraying air pressure 3 kg/cm$^2$, product temperature 30° C., inlet temperature 70° C.) to obtain nicardipine hydrochloride particles.

Separately, 54 g ethyl cellulose (Nissin Chemistry Co.) and 6 g hydroxypropylmethyl cellulose (TC5E, brand name, Shin-Etsu Chemical Co., Ltd.) were dissolved in a mixture of 57 g purified water and 1,083 g methanol. Three-hundred grams nicardipine hydrochloride particles were introduced to a fluidized bed granulator (Freund Industries, uni-glatt) and coated with this solution by side spraying (spraying liquid volume of 8 g/min, spraying air pressure of 2.5 kg/cm$^2$, product temperature of 39° C., inlet temperature of 70° C.) to obtain sustained-release fine particles.

Sixty grams of these sustained-release fine particles, 254.4 g mannitol (Towa Kasei Co., Ltd.) and 63.6 g lactose (Domomilk) that had been pulverized with a pin mill pulverizing device (Hosokawa Micron), and 12 g erythritol (Nikken Chemicals Co., Ltd.) were granulated (spraying liquid volume 15 g/min, spraying air pressure of 0.5 kg/cm$^2$, product temperature of 39° C., inlet temperature of 50° C., spraying cycle of 5 seconds spraying-15 seconds drying) with an aqueous 5% w/w solution containing 8 g copolyvidone (BASF Co., brand name Kollidon VA64) in a fluidized bed granulator (Freund Industries, uni-glatt) to obtain the composition of the present invention. The ratio of ungranulated fine particles was 7.9%.

After further mixing 2 g magnesium stearate with the composition that was obtained, 400 mg tablets containing 20 mg nicardipine hydrochloride per tablet were made under an initial hardness of 0.6 kp using a rotary tableting machine. Next, these tablets were heated for 10 minutes at 130° C. using a program oven (model No. MOV-112P, Sanyo Corporation). Then they were cooled at room temperature for thirty minutes. The tablets that were obtained showed a hardness of 3.7 kp (n=5), friability of 0.1% or less (100 rounds) and disintegration time in the buccal cavity of 20 seconds (n=1). Moreover, as a result of evaluating uniformity of content, CV %=1.1%, proving that there is good uniformity of content. Furthermore, when dissolution of the sustained-release fine particles and tablet was compared 0.5 hour after starting dissolution tests (time when there is approximately 30% dissolution of sustained-release fine particles), 2 hours after (time when there is approximately 50% dissolution of sustained-release fine particles), and 5.5 hours after (time when there is approximately 80% dissolution of sustained-release fine particles) and the difference was calculated, it was 10.3% at 0.5 hour, 12.8% at 2 hours, and 6.6% at 5.5 hours, confirming that acceleration of dissolution of sustained-release fine particles is prevented at any time.

Example 9

Eighty grams tamsulosin hydrochloride and 80 g hydroxypropylmethyl cellulose (TC5E, Shin-Etsu Chemical Co., Ltd.) were dissolved in a mixture of 304 g purified water and 2,736 g methanol. Four-thousand grams Celphere 102 (brand name, Asahi Kasei, mean particle diameter of approximately 127 μm, particle diameter of approximately 50 to approximately 150 μm) were introduced to a fluidized bed granulator (Freund Industries, FLO-5) and coated with this solution by the side spraying method (spraying liquid volume 100 g/min, spraying air pressure 4 kg/cm$^2$, product temperature 40° C., inlet temperature 80° C.) to obtain tamsulosin hydrochloride particles.

Separately, 561.6 g ethyl cellulose (Nissin Chemistry Co., Ltd.) and 158.4 g hydroxypropylmethyl cellulose (TC5E, brand name, Shin-Etsu Chemical Co., Ltd.) were dissolved in a mixture of 564 g purified water and 10,716 g methanol. Four-thousand grams tamsulosin hydrochloride particles were introduced to a fluidized bed granulator (Freund Industries, FLO-5) and coated with this solution by side spraying (spraying liquid volume of 40 g/min, spraying air pressure of 4 kg/cm$^2$, product temperature of 40° C., inlet temperature of 54° C.) to obtain sustained-release fine particles.

Next, 4,000 g of these sustained-release fine particles were introduced to a fluidized bed granulator (Freund Industries, FLO-5) and coated with a mixture of 800 g Aquacoat (brand name, Asahi Kasei), 1,600 g Eudragit L30D55 (brand name, Röhm), 266.7 g Eudragit NE30D (brand name, Röhm), and 5,333 g purified water (spraying liquid volume of 60 g/min, spraying air pressure of 4.5 kg/cm$^2$, product temperature of 50° C., inlet temperature of 84° C.) to obtain enteric sustained-release fine particles.

Then 392.7 g of these enteric sustained-release fine particles and 2,540.2 [g] mannitol (Towa Kasei Co., Ltd.) and 635.1 g lactose (Domomilk) that had been pulverized with a pin mill pulverizing device (Hosokawa Co., Ltd.) were granulated (spraying liquid volume 100 g/min, spraying air pressure of 1.5 kg/cm$^2$, product temperature of 33° C., inlet temperature of 48° C., spraying cycle of 20 seconds spraying-30 seconds drying) with an aqueous 20% w/w solution containing 400 g maltose (Hayashibara Co., Ltd., brand name: Sunmalt S) in a fluidized bed granulator (Freund Industries, FLO-5) to obtain the composition of the present invention. The ratio of ungranulated fine particles was 1.1%.

After further mixing 32 g calcium stearate with the composition that was obtained, 300 mg tablets containing 0.4 mg tamsulosin hydrochloride per tablet were made under an initial hardness of 2.1 kp using a rotary tableting machine. Next, these tablets were kept for 24 hours while heating and humidifying at 25° C./75% RH using a thermostatic chamber at constant humidity (Tabaiespec Co., Ltd., PR-35C). Then they were dried for 3 hours at 30° C. and 40% RH. The tablets that were obtained showed a hardness of 4.1 kp (n=5), friability of 1.67% (100 rounds) and disintegration time in the buccal cavity of 20 seconds (n=1). Moreover, as a result of evaluating uniformity of content, CV %=1.6%, proving that there is good uniformity of content. Furthermore, when dissolution of the sustained-release fine particles and tablet was compared 2 hours after starting dissolution tests (time when there is approximately 30% dissolution of sustained-release fine particles), 4 hours after (time when there is approximately 50% dissolution of sustained-release fine particles), and 8 hours after (time when there is approximately 80% dissolution of sustained-release fine particles) and the difference was calculated, it was 7.5% at 2 hours, 6.4% at 4 hours, and 1.5% at 8 hours, confirming that acceleration of dissolution of sustained-release fine particles is prevented at any time.

INDUSTRIAL APPLICABILITY

The present invention relates to a composition comprising sustained-release fine particles for providing what at a glance are contradictory functions in that the tablets have sustained releasability even though they quickly disintegrate and dissolve in the buccal cavity. Moreover, the present invention is characterized in that it makes it possible to inhibit acceleration of the drug dissolution after making tablets that is the result of destruction of the sustained-release fine particles under tableting pressure when tablets are made, and to realize controlled dissolution, which is the design goal of sustained-release fine particle preparation, with good reproducibility, even after tablets have been made. Therefore, pharmaceutical preparation design of the sustained-release fine particles is simplified, and there is further the characteristic of making it possible to guarantee good uniformity of drug content. Furthermore, it is possible to present a composition comprising sustained-release fine particles that will have a profound effect in the development of an assortment of quick-disintegrating tablets in the buccal cavity during the step of making the quick-disintegrating tablets in the buccal cavity comprising sustained-release fine particles into a product, particularly during the step of industrial manufacture, and further, the step of quality assurance.

What is claimed is:

1. A method of manufacturing a composition comprising sustained-release fine particles, said method comprising:
    providing sustained-release fine particles having controlled dissolution for quick-disintegrating tablets in the buccal cavity, wherein each particle comprises a coated drug over a core selected from the group consisting of microcrystalline cellulose, sodium chloride and silicon dioxide, and further a coating of a polymer substance over the drug; and
    granulating by intermittent spraying said sustained-release fine particles and one or two or more fillers selected from the group consisting of sugars and sugar alcohols together with a binder for quick-disintegrating tablets in the buccal cavity, and wherein the ratio of ungranulated sustained-release fine particles in the entire composition is 0 to 15% and the coefficient of variation (CV %) of the amount of drug is 3.5% or less, wherein the mean particle diameter of the sustained-release fine particles is approximately 0.1 µm to approximately 350 µm to produce said composition;

wherein the binder for quick-disintegrating tablets in the buccal cavity is one or two or more selected from the group consisting of saccharides of high moldability, water-soluble polymer substances, and saccharides with a low melting point, and wherein the sugar or sugar alcohol is one or two or more selected from the group consisting of saccharides with low moldability, saccharides with a high melting point, and saccharides with a low melting point.

2. The method of manufacturing a composition comprising sustained-release fine particles for quick-disintegrating tablets in the buccal cavity of claim 1, wherein the mixture ratio of sustained-release fine particles, filler, and binder for quick-disintegrating tablets in the buccal cavity is 1 to 50%, 20 to 98%, and 1 to 30%, respectively.

3. The method of manufacturing a composition comprising sustained-release fine particles for quick-disintegrating tablets in the buccal cavity of claim 1, wherein the sustained-release fine particles consist of at least crystal cellulose particles, drug, and polymer substance.

4. The method of manufacturing a composition comprising sustained-release fine particles for quick-disintegrating tablets in the buccal cavity of claim 3, wherein the drug is tamsulosin hydrochloride.

5. The method of manufacturing composition comprising sustained-release fine particles for quick-disintegrating tablets in the buccal cavity of claim 1 or 3, wherein the sustained-release fine particles are enteric sustained-release fine particles.

6. The method of manufacturing a composition comprising sustained-release fine particles for quick-disintegrating tablets in the buccal cavity of claim 1 or 3, wherein the polymer substances is selected from the group consisting of hydroxypropylmethyl cellulose, ethyl cellulose, methacrylic acid-ethyl acrylate copolymer and ethyl acrylate-methyl methacrylate copolymer dispersion.

7. The method of manufacturing a composition comprising sustained-release fine particles for quick-disintegrating tablets in the buccal cavity of claim 1, wherein the binder for quick-disintegrating tablets in the buccal cavity is one or two or more selected from the group consisting of maltose, trehalose, sorbitol, and maltitol.

8. A method of manufacturing quick-disintegrating tablets in the buccal cavity consisting of the composition comprising sustained-release fine particles of claim 7.

* * * * *